United States Patent [19]

Van Daele et al.

[11] Patent Number: 5,602,129
[45] Date of Patent: Feb. 11, 1997

[54] N-(3-HYDROXY-4-PIPERIDINYL)(DIHYDROBENZOFURAN, DIHYDRO-2H-BENZOPYRAN OR DIHYDROBENZODIOXIN)CARBOXAMIDE DERIVATIVES

[75] Inventors: Georges H. P. Van Daele, Turnhout; Frans M. A. Van den Keybus, Essen, both of Belgium

[73] Assignee: Janssen Pharmaceutica N.V., Beerse, Belgium

[21] Appl. No.: 421,727

[22] Filed: Apr. 13, 1995

Related U.S. Application Data

[62] Division of Ser. No. 301,825, Sep. 7, 1994, Pat. No. 5,552,553, which is a division of Ser. No. 489,419, Mar. 6, 1990, Pat. No. 5,374,637, which is a continuation-in-part of Ser. No. 326,941, Mar. 22, 1989, abandoned.

[51] Int. Cl.$^6$ .................. A61K 31/53; C07D 403/14
[52] U.S. Cl. .................. 514/241; 514/252; 514/274; 514/316; 514/326; 544/212; 544/238; 544/315; 544/316; 544/317; 546/196; 546/197; 546/188
[58] Field of Search .................. 546/208, 210, 546/188, 196, 197; 514/326, 274, 316, 252, 241; 544/315, 316, 317, 238, 212

[56] References Cited

U.S. PATENT DOCUMENTS

| | | | |
|---|---|---|---|
| 4,434,170 | 2/1984 | Dostert et al. | 424/265 |
| 4,772,459 | 9/1988 | Sun et al. | 424/10 |

FOREIGN PATENT DOCUMENTS

| | | |
|---|---|---|
| 68700 | 1/1983 | European Pat. Off. . |
| 76530 | 4/1983 | European Pat. Off. . |
| 124783 | 11/1984 | European Pat. Off. . |
| 147044 | 7/1985 | European Pat. Off. . |
| 234872 | 9/1987 | European Pat. Off. . |
| 299566 | 1/1989 | European Pat. Off. . |
| 309043 | 3/1989 | European Pat. Off. . |
| 307172 | 3/1989 | European Pat. Off. . |

*Primary Examiner*—Joseph McKane
*Assistant Examiner*—Richard S. Myers, Jr.
*Attorney, Agent, or Firm*—Charles J. Metz

[57] ABSTRACT

N-(3-hydroxy-4-piperidinyl)(dihydrobenzofuran, dihydro-2H-benzopyran or dihydrobenzodioxin)carboxamide derivatives, their N-oxide forms and pharmaceutically acceptable salts having gastrointestinal motility stimulating properties, compositions containing these compounds as active ingredient and methods of treating warm-blooded animals suffering from the decreased peristalsis of the gastrointestinal system.

30 Claims, No Drawings

N-(3-HYDROXY-4-PIPERIDINYL)(DIHYDRO-BENZOFURAN, DIHYDRO-2H-BENZOPYRAN OR DIHYDROBENZODIOXIN)CARBOXAMIDE DERIVATIVES

CROSS-REFERENCE TO RELATED APPLICATION

This is a division of application Ser. No. 08/301,825, filed Sep. 7, 1994, now U.S. Pat. No. 5,552,553 which was a division of application Ser. No. 07/489,419, filed Mar. 6, 1990, now U.S. Pat. No. 5,374,637, which was a continuation-in-part of application Ser. No. 07/326,941, filed Mar. 22, 1989, now abandoned.

BACKGROUND OF THE INVENTION

A number of substituted (3-hydroxy-4-piperidinyl)benzamide derivatives have been described as stimulators of the motility of the gastrointestinal system in EP-A-0,076,530, EP-A-0,299,566 and EP-A-0,309,043.

In EP-A-0,307,172; EP-A-0,124,783; DE-3,702,005; EP-A-0,147,044; EP-A-0,234,872 and U.S. Pat. No. 4,772,459 there are described benzofuran, benzopyran or benzoxepin carboxamide derivatives being substituted on the nitrogen with an alkylamino group or with a mono- or bicyclic hetero ring optionally through an alkyl chain. These compounds are taught to be anti-emetic, anti-psychotic or neuroleptic agents.

In the EP-A-0,068,700; BE-0,890,962; FR-2,396,757 there are described dihydrobenzodioxin carboxamide derivatives being substituted on the nitrogen with a mono- or bicyclic hetero ring. These compounds are claimed to be useful in the treatment of disorders of the central nervous system and as anti-emetic agents.

The N-(3-hydroxy-4-piperidinyl)(dihydrobenzofuran, dihydro-2H-benzopyran or dihydrobenzodioxin)carboxamide derivatives of the present invention differ therefrom structurally and pharmacologically by their favourable gastrointestinal motility stimulating properties. In particularly the present compounds show unexpected motility enhancing effects on the colon.

DESCRIPTION OF THE INVENTION

The present invention is concerned with novel benzamide derivatives having the formula

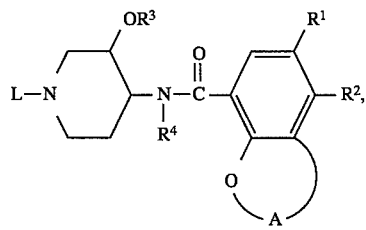

the N-oxide forms, the salts and the stereochemically isomeric forms thereof, wherein:

A is a radical of formula $-CH_2-CH_2-$ (a-1), $-CH_2-CH_2-CH_2-$ (a-2), $-CH_2-CH_2-CH_2-CH_2-$ (a-3), $-CH_2-O-$ (a-4), $-CH_2-CH_2-O-$ (a-5), or $-CH_2-CH_2-CH_2-O-$ (a-6), wherein one or two hydrogen atoms in said radicals (a-1) to (a-6) may be replaced by a $C_{1-6}$alkyl radical;

$R^1$ is hydrogen, halo, $C_{1-6}$alkylsulfonyl or aminosulfonyl;

$R^2$ is hydrogen, amino, mono or di($C_{1-6}$alkyl)amino, aryl$C_{1-6}$alkylamino or $C_{1-6}$alkylcarbonylamino;

$R^3$ and $R^4$ are each independently hydrogen or $C_{1-6}$alkyl;

L is $C_{3-6}$cycloalkyl, $C_{5-6}$cycloalkanone, $C_{3-6}$alkenyl optionally substituted with aryl, or L is a radical of formula $-Alk-R^5$ (b-1), $-Alk-X-R^6$ (b-2), $-Alk-Y-C(=O)-R^8$ (b-3), or $-Alk-Y-C(=O)-NR^{10}R^{11}$ (b-4), wherein each Alk is $C_{1-6}$alkanediyl; and $R^5$ is hydrogen, cyano, $C_{1-6}$alkylsulfonylamino, $C_{1-6}$cycloalkyl, $C_{5-6}$cycloalkanone, aryl, di(aryl)methyl or Het;

$R^6$ is hydrogen, $C_{1-6}$alkyl, $C_{3-6}$cycloalkyl, aryl or Het;

X is O, S, $SO_2$ or $NR^7$; said $R^7$ being hydrogen, $C_{1-6}$alkyl or aryl;

$R^8$ is hydrogen, $C_{1-6}$alkyl, $C_{3-6}$cycloalkyl, aryl, aryl$C_{1-6}$alkyl, di(aryl)methyl or $C_{1-6}$alkyloxy;

Y is $NR^9$ or a direct bond; said $R^9$ being hydrogen, $C_{1-6}$alkyl or aryl;

$R^{10}$ and $R^{11}$ each independently are hydrogen, $C_{1-6}$alkyl, $C_{3-6}$cycloalkyl, aryl or aryl$C_{1-6}$alkyl, or $R^{10}$ and $R^{11}$ combined with the nitrogen atom bearing $R^{10}$ and $R^{11}$ may form a pyrrolidinyl or piperidinyl ring both being optionally substituted with $C_{1-6}$alkyl, amino or mono or di($C_{1-6}$alkyl)amino, or said $R^{10}$ and $R^{11}$ combined with the nitrogen bearing $R^{10}$ and $R^{11}$ may form a piperazinyl or 4-morpholinyl radical both being optionally substituted with $C_{1-6}$alkyl;

each aryl being unsubstituted phenyl or phenyl substituted with 1,2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and each Het being a five- or six-membered heterocyclic ring containing 1,2,3 or 4 heteroatoms selected from oxygen, sulfur and nitrogen, provided that no more than 2 oxygen and/or sulfur atoms are present, said five- or six-membered ring being optionally condensed with a five- or six-membered carboxylic or heterocyclic ring also containing 1,2,3 or 4 heteroatoms selected from oxygen, sulfur and nitrogen, provided that the latter ring does not contain more than 2 oxygen and/or sulfur atoms and that the total number of heteroatoms in the bicyclic ring system is less than 6; when Her is a monocyclic ring system it may optionally be substituted with up to 4 substituents; when Het is a bicyclic ringsystem it may optionally be substituted with up to 6 substituents; said substituents being selected from the group consisting of halo, hydroxy, cyano, trifluoromethyl, $C_{1-6}$alkyl, aryl $C_{1-6}$alkyl, aryl, $C_{1-6}$ alkyloxy, $C_{1-6}$alkyloxy$C_{1-6}$alkyl, hydroxy$C_{1-6}$alkyl, $C_{1-6}$alkylthio, mercapto, nitro, amino, mono and di ($C_{1-6}$alkyl)amino, aryl $C_{1-6}$alkylamino, aminocarbonyl, mono and di($C_{1-6}$alkyl)aminocarbonyl, $C_{1-6}$alkyloxycarbonyl, aryl$C_{1-6}$alkyloxycarbonyl, a bivalent radical =O and =S; provided that when $R^6$ is Het, Het is connected to X on a carbon atom.

As used in the foregoing definitions "halo" is genetic to fluoro, chloro, bromo and iodo; "$C_{1-6}$alkyl" defines straight and branch chained saturated hydrocarbon radicals having from 1 to 6 carbon atoms such as, for example, methyl, ethyl, propyl, butyl, hexyl, 1-methylethyl, 2-methylpropyl and the like; "$C_{3-6}$cycloalkyl" is genetic to cyclopropyl, cyclobutyl, cyclopentyl and cyclohexyl; "$C_{5-6}$cycloalkanone" is generic to cyclopentanone and cyclohexanone; "$C_{3-6}$alkenyl" defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and when a $C_{3-6}$alkenyl is substituted on a heteroatom, then the carbon atom of said $C_{3-6}$alkenyl connected to said heteroatom preferably is saturated; "$C_{1-6}$alkanediyl" defines bivalent straight or branch chained hydrocarbon radicals containing from 1 to 6 carbon atoms such as, for example, 1,2-ethanediyl, 1,3-propanediyl, 1,4-butanediyl, 1,5-pentanediyl, 1,6-hexanediyl and the branched isomers thereof.

The salts as mentioned hereinabove are meant to comprise the therapeutically active non-toxic addition salt forms which the compounds of formula (I) are able to form. The latter can conveniently be obtained by treating the base form with such appropriate-acids as inorganic acids, for example, hydrohalic acids, e.g. hydrochloric, hydrobromic and the like, sulfuric acid, nitric acid, phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be convened by treatment with alkali into the free base form.

The compounds of formula (I) containing acidic protons may aim be convened into their therapeutically active non-toxic metal or amine salt forms by treatment with appropriate organic or inorganic bases.

The term addition salt also comprises the hydrates and solvent addition forms which the compounds of formula (I) are able to form. Examples of such forms are e.g. hydrates, alcoholates and the like.

The N-oxides of the compounds of formula (I) are meant to comprise those compounds of formula (I) wherein one or several nitrogen atoms are oxidated to the N-oxide form, in particularly those N-oxides wherein the piperidine-nitrogen is N-oxidated.

The compounds of formula (I) have at least two asymmetric carbon atoms in their structure, namely those located in the 3- and the 4-position of the piperidine nucleus. It is evident that the stereochemically isomeric forms of the compounds of formula (I) are intended to be embraced within the scope of the invention. Furthermore the compounds of the present invention may form cis/trans isomers, more particularly, the substituents in said 3- and 4-positions of the piperidine nucleus may have either a trans or cis configuration; and such cis/trans isomers too are intended to be within the scope of the present invention.

In the compounds of formula (I) wherein $R^5$ and $R^6$ is Het, said Het may be partly or completely saturated, or unsaturated. The compounds of formula (I) wherein Het is partly saturated or unsaturated and is substituted with hydroxy, mercapto or amino, may also exist in their tautomeric forms. Such forms although not explicitly indicated hereinabove, are intended to be included within the scope of the invention.

In particular, Het may be:

i) an optionally substituted five- or six-membered heterocyclic ring containing 1,2,3 or 4 heteroatoms selected from oxygen, sulfur and nitrogen, provided that no more than 2 oxygen and/or sulfur atoms are present; or ii) an optionally substituted five- or six-membered heterocyclic ring containing 1,2 or 3 heteroatoms selected from oxygen, sulfur and nitrogen, being fused with an optionally substituted five- or six-membered ring through 2 carbon atoms or 1 carbon and 1 nitrogen atom, containing in the remainder of the fused ring only carbon atoms; or iii) an optionally substituted five- or six-membered heterocyclic ring containing 1,2 or 3 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;

wherein Het being a monocyclic ring system may be optionally substituted with up to 4 substituents; and wherein Het being a bicyclic ring system may be optionally substituted with up to 6 substituents, said substituents being the same as defined hereinabove.

A more particular subgroup of Het comprises cyclic ether or thioether ring systems containing one or two oxygen and/or sulfur atoms, provided that when two oxygen and/or sulfur atoms are present, they are in non-adjacent positions in the ring. Said cyclic ether or thioether ring systems are optionally condensed with a five- or six-membered carbocyclic ring. These cyclic ether or thioether ring systems may also be substituted with one or more $C_{1-6}$alkyl, $C_{1-6}$alkyloxy, $C_{1-6}$alkyloxy$C_{1-6}$alkyl or hydroxy-$C_{1-6}$alkyl substituents. This subgroup of Het radicals will be represented by the symbol $Het^1$.

Typical cyclic ethers and thioethers which are covered by $R^5$ being Het in the compounds of the present invention can be represented by the following formulae:

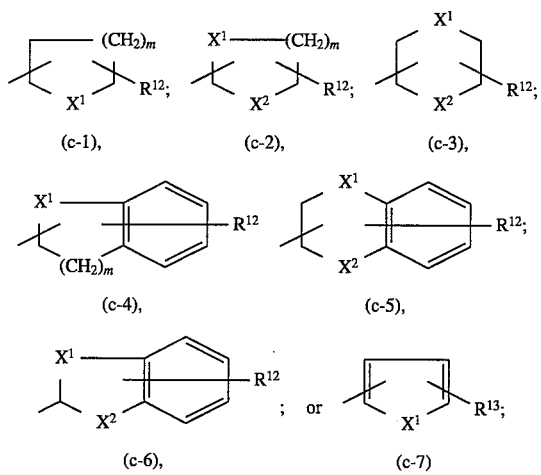

wherein each $X^1$ and $X^2$ each independently are O or S; m is 1 or 2; each $R^{12}$ is hydrogen, $C_{1-4}$alkyl, $C_{1-4}$alkyloxy$C_{1-4}$alkyl or hydroxy$C_{1-4}$alkyl and $R^{13}$ is hydrogen, halo or $C_{1-4}$alkyl.

Further particular cyclic ethers are selected from the group consisting of 1,3-dioxolanyl optionally substituted with $C_{1-4}$alkyl, 1,3-dioxanyl optionally substituted with $C_{1-4}$alkyl, tetrahydrofuranyl optionally substituted with C1.4alkyl, tetrahydropyranyl optionally substituted with $C_{1-4}$alkyl, 2,3-dihydro-1,4-benzodioxinyl, 2,3-dihydrobenzofuran and 3,4-dihydro-1(2H)-benzopyranyl, with tetrahydrofuranyl being preferred.

Another more particular subgroup of Het comprises heterocyclic ring systems which are selected from the group consisting of pyridinyl which is optionally substituted with one or two substituents each independently selected from halo, hydroxy, cyano, $C_{1-6}$alkyl, trifluoromethyl, $C_{1-6}$alkyloxy, aminocarbonyl, mono and di($C_{1-6}$alkyl)aminocarbonyl, amino, mono and di($C_{1-6}$alkyl)amino and $C_{1-6}$alkyloxycarbonyl; pyrimidinyl which is optionally substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl Which is optionally substituted with $C_{1-6}$alkyl or halo; pyrazinyl which is optionally substituted with one ore two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl; pyrrolyl which is optionally substituted with $C_{1-6}$alkyl; pyrazolyl which is optionally substituted with $C_{1-6}$alkyl; imidazolyl which is optionally substituted with $C_{1-6}$alkyl; triazolyl which is optionally substituted with $C_{1-6}$alkyl; quinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; isoquinolinyl optionally substituted with up to two substituents each independently selected from halo, hydroxy, cyano, $C_{1-6}$alkyl, $C_{1-6}$alkyloxy, amino, mono and di($C_{1-6}$alkyl)amino and trifluoromethyl; quinoxalinyl optionally substituted with up to two substituents each independently selected from $C_{1-6}$alkyl, hydroxy, halo, cyano and $C_{1-6}$alkyloxy; quinazolinyl optionally substituted with $C_{1-6}$alkyl; benzimidazolyl optionally substituted with $C_{1-6}$alkyl; indolyl optionally substituted with $C_{1-6}$alkyl; 5,6,7,8-tetrahydroquinolinyl optionally substituted with up to two substituents each independently selected from halo, hydroxy, cyano, $C_{1-6}$alkyl, $C_{1-6}$alkyloxy, amino, mono- and di($C_{1-6}$alkyl)amino and trifluoromethyl; 5,6,7,8-tetrahydroquinoxalinyl optionally substituted with up to taro substituents each independently selected from $C_{1-6}$alkyl, hydroxy, halo, cyano and $C_{1-6}$alkyloxy; thiazolyl optionally substituted with $C_{1-6}$alkyl; oxazolyl optionally substituted with $C_{1-6}$alkyl; benzoxazolyl optionally substituted with $C_{1-6}$alkyl; benzothiazolyl optionally substituted with $C_{1-6}$alkyl. This subgroup of Het radicals will be represented by the symbol $Het^2$.

Further particular heterocyclic ring systems within this subgroup are ring systems wherein Het is an optionally substituted six-membered aromatic ring such as, for example, pyridinyl optionally substituted with up to two substituents selected from $C_{1-4}$alkyl, cyano, halo and trifluoromethyl; pyrimidinyl, optionally substituted with up to two substituents selected from hydroxy, amino, mono and di($C_{1-4}$alkyl)amino and $C_{1-4}$alkyl; pyrazinyl optionally substituted with cyano, halo, $C_{1-4}$alkyloxycarbonyl and $C_{1-4}$alkyl ; and pyridazinyl optionally substituted with halo.

Another more particular subgroup of Het comprises optionally substituted five- or six-membered cyclic amides containing one, two or three nitrogen atoms, said five or six-membered heterocyclic ring being optionally condensed with a five- or six-membered carbocyclic or heterocyclic ting containing one or two nitrogen atoms or one sulfur or oxygen atom. This subgroup of Het will be represented hereinafter by the symbol $Het^3$.

Typical monocyclic amides covered by $R^5$ and $R^6$ being Het in the compounds of the present invention, can be represented by the following formulae:

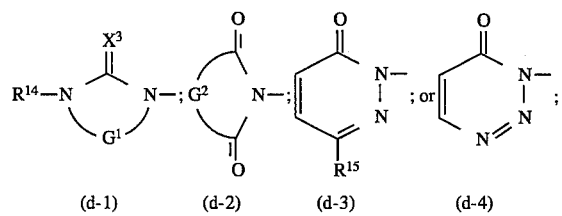

(d-1)   (d-2)   (d-3)   (d-4)

wherein $X^3$ is O or S;

$R^{14}$ is hydrogen, $C_{1-6}$alkyl or aryl$C_{1-6}$alkyl;

$R^{15}$ is hydrogen, halo, $C_{1-6}$alkyl or aryl;

$G^1$ is —$CH_2$—$CH_2$—, —CH=CH—, —N=N—, —C(=O)—$CH_2$— or —$CH_2$—$CH_2$—$CH_2$—, wherein one or two hydrogen atoms each independently may be replaced by $C_{1-6}$alkyl; and $G^2$ is —$CH_2$—$CH_2$—, —$CH_2$—N($R^{14}$)—or —$CH_2$—$CH_2$—$CH_2$, wherein one or two hydrogen atoms each independently may be replaced by $C_{1-6}$alkyl.

Typical bicyclic amides covered by the definition of $R^5$ and $R^6$, can be represented by the following formulae:

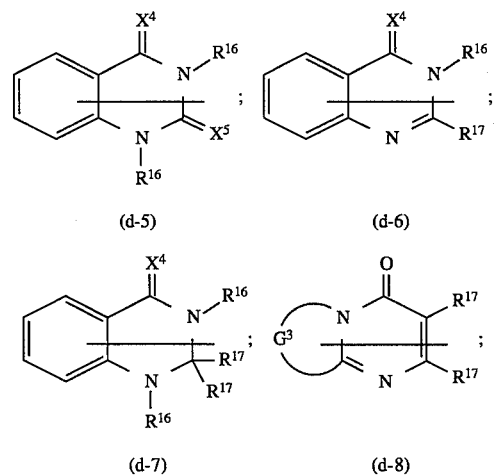

(d-5)   (d-6)

(d-7)   (d-8)

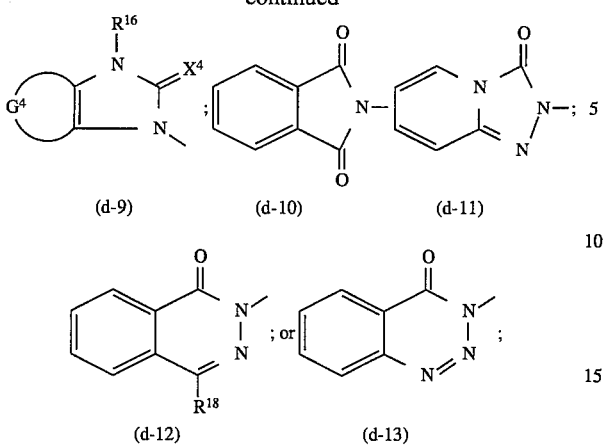

wherein
$X^4$ and $X^5$ each independently are O or S;

each $R^{16}$ independently is hydrogen, $C_{1-6}$alkyl or aryl$C_{1-6}$alkyl;

each $R^{17}$ independently is hydrogen, halo, $C_{1-6}$alkyl or $C_{1-6}$alkyloxy; and $R^{18}$ is hydrogen, halo, $C_{1-6}$alkyl or aryl;

wherein the radicals (d-5), (d-6), (d-7) and (d-8) may be connected to respectively Alk or X by replacing either a hydrogen or a radical $R^{16}$ and $R^{17}$ by a free bond;

$G^3$ is —CH=CH—CH=CH—, —(CH$_2$)$_4$—, —S—(CH$_2$)$_2$—, —S—(CH$_2$)$_3$—, —S—CH=CH—, —CH=CH—O—, —NH—(CH$_2$)$_2$—, —NH—(CH$_2$)$_3$—, —NH—CH=CH—, —NH—N=CH—CH$_2$—, —NH—CH=N— or —NH—N=CH—;

$G^4$ is —CH=CH—CH=CH—, —CH=CCl—CH=CH—, —CCl=CH—CH—, —N=CH—CH=CH—, —CH=N—CH=CH—, —CH=CH—N=CH—, —CH=CH—CH=N—, —N=CH—N=CH— or —CH=N—CH=N—.

Further particular heterocyclic ring systems within this subgroup are selected from the group consisting of 2,3-dihydro-2-oxo-1H-benzimidazolyl optionally substituted with $C_{1-6}$alkyl; 2-oxo-1-imidazolidinyl optionally substituted with $C_{1-4}$alkyl; 2,5-dioxo-1-imidazolidinyl optionally substituted with $C_{1-4}$alkyl; 3,4-dihydro-4-oxo-1,2,3-benzotriazin-3-yl; 1-oxo-2(1H)-phthalazinyl; 2,3-dihydro-5-oxo-5H-thiazolo-[3,2-a]-pyrimidin-6-yl optionally substituted with $C_{1-4}$alkyl; and 5-oxo-5H-thiazolo-[3,2-a]-pyrimidin-6-yl optionally substituted with $C_{1-4}$alkyl.

Preferred compounds within the invention are those compounds of formula (I) wherein $R^1$ is hydrogen or halo; and/or $R^2$ is hydrogen or amino; and/or $R^3$ is hydrogen or $C_{1-4}$alkyl; and/or $R^4$ is hydrogen; and/or L is a radical of formula (b-1) wherein $R^5$ is hydrogen, $C_{3-6}$cycloalkyl, $C_{5-6}$cycloalkanone, aryl or Het; or L is a radical of formula (b-2) wherein X is O, S or NH and $R^6$ is hydrogen, $C_{1-4}$alkyl, aryl or Het; or L is a radical of formula (b-3) wherein Y is NH or a direct bond and $R^8$ is hydrogen, $C_{1-4}$alkyl, aryl or $C_{1-4}$alkyloxy; or L is a radical of formula (b-4) wherein Y is NH or a direct bond and $R^{10}$ and $R^{11}$ each independently are hydrogen, $C_{1-4}$alkyl or aryl, or $R^{10}$ and $R^{11}$ combined with the nitrogen bearing said $R^{10}$ and $R^{11}$ may form a pyrrolidinyl or piperidinyl radical.

More preferred compounds are those preferred compounds wherein the substituents on the 3 and 4 position of the piperidine ring have the cis-configuration.

Particular preferred compounds are those more preferred compounds wherein $R^1$ is halo, $R^2$ is amino, $R^3$ is $C_{1-4}$alkyl, $R^4$ is hydrogen and A is a radical of formula (a-1) or (a-2) wherein the carbon atom adjacent to the oxygen atom is optionally substituted with one or two $C_{1-4}$alkyl substituents.

Other particular preferred compounds are those more preferred compounds wherein $R^1$ is halo, $R^2$ is amino, $R^3$ is $C_{1-4}$alkyl, $R^4$ is hydrogen and A is a radical of formula (a-5).

Most preferred compounds are selected from the group consisting of cis-4-amino-5-chloro-2,3-dihydro-N-[3-methoxy-1-[2-(1-oxo-2(1H)phthalazinyl)ethyl]4-piperidinyl]-7-benzofurancarboxamide, cis-4-amino-5-chloro-2,3-dihydro-N-[3-methoxy-1-[(tetrahydro-2-furanyl)methyl]-4-piperidinyl]-7-benzofurancarboxamide, cis-4-amino-5-chloro-N-[1-[3-(3-ethyl-2,3-dihydro-2-oxo-1H-benzimidazol-1-yl)propyl]-3-methoxy-4-piperidinyl]-2,3-dihydro-7-benzofurancarboxamide, cis-4-amino-5-chloro-N-[1-(2-cyclohexylethyl)-3-methoxy-4-piperidinyl]-2,3-dihydro-7-benzofurancarboxamide, cis-4-amine-5-chloro-N-(1-ethyl-3-methoxy-4-piperidinyl)-2,3-dihydro-7-benzofurancarboxamide, cis-4-amino-5-chloro-N-[1-[2-(2,3-dihydro-7-methyl-5-oxo-5H-thiazolo[3,2-a]pyrimidin-6-yl)ethyl]-3-methoxy-4-piperidinyl]-2,3-dihydro-7-benzofurancarboxamide, cis-4-amino-5-chloro-2,3-dihydro-N-[3-methoxy-1-[3-(1-methylethoxy)propyl]-4-piperidinyl]-7-benzofurancarboxamide, cis-4-amino-5-chloro-2,3-dihydro-N-(3-methoxy-1-methyl-4-piperidinyl)-7-benzofurancarboxamide, the pharmaceutically acceptable acid addition salts and the stereochemically isomeric forms thereof, or from the group selected from cis-5-amino-6-chloro-N-(1-ethyl-3-methoxy-4-piperidinyl)-3,4-dihydro-2H-1-benzopyran-8-carboxamide, cis-5-amino-6-chloro-3,4-dihydro-N-[3-methoxy-1-[2-(1-methylethoxy)ethyl]-4-piperidinyl]-2H-1-benzopyran-8-carboxamide, cis-5-amino-6-chloro-3,4-dihydro-N-[3-methoxy-1-[3-(1-methylethoxy)propyl]-4-piperidinyl]-2H-1-benzopyran-8-carboxamide, the pharmaceutically acceptable acid addition salts and the stereochemically isomeric forms thereof, or from the group selected from cis-5-amino-6-chloro-3,4-dihydro-N-[3-methoxy-1-[(tetrahydro-2-furanyl)methyl]-4-piperidinyl]-2H-1-benzopyran-8-carboxamide, cis-8-amino-7-chloro-N-[1-[3-(3-ethyl-2,3-dihydro-2-oxo-1H-benzimidazol-1-yl)propyl]-3-methoxy-4-piperidinyl]-2,3-dihydro-1,4-benzodioxin-5-carboxamide, the pharmaceutically acceptable acid addition salts and the stereochemically isomeric forms thereof.

In order to simplify the structural representations of the compounds of formula (I) and of certain starting materials and intermediates thereof, the radical will hereafter be represented by the symbol D.

The compounds of formula (I) can be prepared by N-alkylating a piperidine of formula (II) with an intermediate of formula (III).

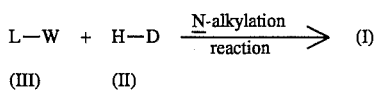

W as described in the reaction of (III) with (II) and in the following reaction schemes is an appropriate leaving group such as, for example, halo, preferably, chloro, bromo or iodo, or a sulfonyloxy group, e.g. methanesulfonyloxy, 4-methylbenzenesulfonyloxy and the like leaving groups.

The N-alkylation reaction of (II) with (III) is conveniently conducted in a reactioninert solvent such as, for example, water, an aromatic hydrocarbon, e.g. benzene, methylbenzene, dimethylbenzene, chlorobenzene, methoxybenzene and the like, an alkanol, e.g. methanol, ethanol, 1-butanol and the like, a halogenated hydrocarbon, e.g. dichloromethane, trichloromethane and the like, an ester, e.g. ethyl acetate, γ-butyrolactone and the like, a ketone, e.g. 2-propanone, 4-methyl-2-pentanone and the like, an ether, e.g. 1,4-dioxane, 1,1'-oxybisethane, tetrahydrofuran and the like, a polar aprotic solvent, e.g. N,N-dimethylformamide, N,N-dimethylacetamide, dimethylsulfoxide, hexamethylphosphor triamide, 1,3-dimetyl-3,4,5,6-tetrahydro-2(1H)-pyrimidinone, 1,3-dimethyl-2-imidazolidinone, 1,1,3,3,-tetramethylurea, nitrobenzene, 1methyl-2-pyrrolidinone and the like, or a mixture of such solvents.

The addition of an appropriate base such as, for example, an alkali or an earth alkaline metal carbonate, hydrogen carbonate, carboxylate, amide, oxide, hydroxide or alkoxide, e.g. sodium carbonate, sodium hydrogen carbonate, potassium carbonate, calcium oxide, sodium acetate, sodium amide, sodium hydroxide, sodium methoxide and the like or an organic base such as, for example, an amine, e.g. N,N-dimethyl-4-pyridinamine, N,N-diethylethanamine, N-(1-methylethyl)-2-propanamine, 1,4-diazabicyclo-[2,2,2]octane, 4-ethylmorpholine and the like, may be utilized to pick up the acid which is liberated during the course of the reaction. In some instances the addition of a iodide salt, preferably an alkali metal iodide, or a crown ether, e.g. 1,4,7,10,13,16-hexaoxacyclooctadecane and the like, may be appropriate. Stirring and somewhat elevated temperatures may enhance the rate of the reaction. Additionally, it may be advantageous to conduct said N-alkylation under an inert atmosphere such as, for example, oxygen-free argon or nitrogen gas. Alternatively, said N-alkylation may be carried out by applying art-known conditions of phase transfer catalysis reactions. Said conditions comprise stirring the reactants, with an appropriate base and optionally under an inert atmosphere as defined hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfate and the like catalysts. Somewhat elevated temperatures may be appropriate to enhance the rate of the reaction.

In this and the following preparations, the reaction products may be isolated from the reaction mixture and, if necessary, further purified according methodologies generally known in the art such as, for example, extraction, distillation, crystallization, tituration and chromatography.

The compounds of formula (I) can also be prepared by the amidation reaction of an amine of formula

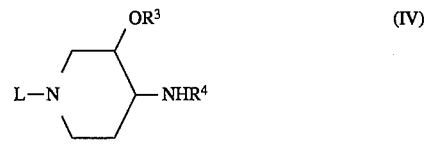

with a carboxylic acid of formula

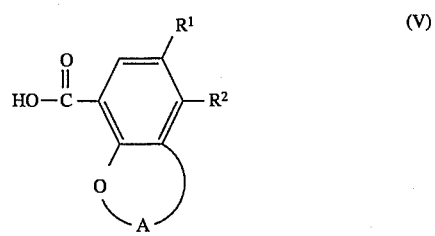

or a functional derivative thereof, such as a halide, a symmetrical or mixed anhydride or an ester, preferably an activated ester. Said functional derivative may be generated in situ, or if desired, be isolated and further purified before reacting it with the amine of formula (IV). Functional derivatives may be prepared following art-known procedures, for example, by reacting the carboxylic acid of formula (V) with thionyl chloride, phosphorous trichloride, phosphoryl chloride and the like, or by reacting the carboxylic acid of formula (V) with an acyl halide, e.g. acetyl chloride, ethyl carbonochloridate and the like. Or the intermediates (IV) and (V) may be coupled in the presence of a suitable reagent capable of forming amides, e.g. dicyclohexylcarbodiimide, 2-chloro-1-methylpyridinium iodide and the like.

Said amidation reactions may conveniently be carried out by stirring the reactants in a suitable reaction-inert solvent such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a dipolar aprotic solvent, e.g. N,N-dimethylformamide, N,N-dimethylacetamide and the like. The addition of a suitable base may be appropriate, in particular a tertiary amine such as, N,N-diethylethanamine. The water, the alcohol or the acid which is liberated during the course of the reaction may be removed from the reaction mixture according to methodologies generally known in the an such as, for example, azeotropical distillation, complexation or salt formation. In some instances it may be advantageous to cool the reaction mixture. Further it may be expedient to protect amino or hydroxy groups during the course of the reaction to avoid undesired side reactions. Suitable protecting groups comprise readily removable groups such as, $C_{1-6}$alkylcarbonyl, $C_{1-4}$alkyloxycarbonyl, arylmethyl, tertiair butyl and the like protective groups.

The compounds of formula (I) can alternatively be prepared by the reductive N-alkylation reaction of an appropriate ketone or aldehyde of formula L'=O (VI), said L'=O being a compound of formula L-H wherein two geminal hydrogen atoms in the $C_{1-6}$alkanediyl or $C_{3-6}$cycloalkanediyl moiety are replaced by =O, with a piperidine of formula H-D (II).

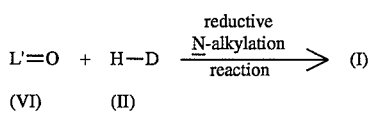

Said reductive N-alkylation reaction may conveniently be carried out by reducing a mixture of the reactants in a suitable reaction-inert solvent In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethylacetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic-acids, e.g. acetic acid, propanoic acid and the like; or a mixture of such solvents. The term "art-known reductive N-alkylation procedures" means that the reaction is carried out either with sodium cyanoborohydride, sodium borohydride, formic acid or a salt thereof, e.g. ammonium formate and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

The compounds of formula (I) wherein L is a radical of formula (b-2) and $R^6$ is Het can alternatively be prepared according to one of the following alkylation procedures.

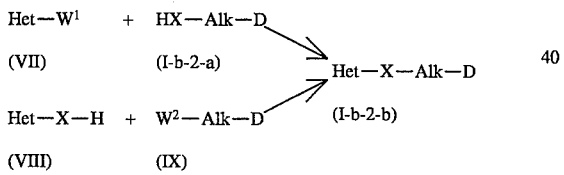

In (VII) and (IX) $W^1$ and $W^2$ are appropriate leaving groups such as, for example, a halo, e.g. chloro or bromo, a $C_{1-6}$alkyloxy or a $C_{1-6}$alkylthio, e.g. methoxy or methylthio in case of $W^1$, or a sulfonyloxygroup or pyridinium group in case of $W^2$.

The alkylation reactions of (VII) with (I-b-2-a) and (VIII) with (IX) can be carried out according to art-known procedures, e.g. by stirring the reactants without a solvent or in an inert organic solvent such as, for example, an aromatic hydrocarbon, e.g. benzene, methylbenzene, dimethylbenzene, and the like, a lower alkanol, e.g. methanol, ethanol, 1-butanol and the like, a ketone, e.g. 2-propanone, 4-methyl-2-pentanone and the like, an ether, e.g. 1,4-dioxane, 1,1'-oxybisethane, tetrahydrofuran and the like, a polar aprotic solvent, e.g. N,N-dimethylformamide, N,N-dimethylacetamide, dimethylsulfoxide, nitrobenzene, 1-methyl-2-pyrrolidinone and the like or a mixture of two or more of such solvents. The addition of an appropriate base such as, for example, an alkali or an earth alkaline metal carbonate, hydrogen carbonate, hydroxide, alkoxide, hydride, amide or oxide, e.g. sodium carbonate, sodium hydrogen carbonate, potassium carbonate, sodium hydroxide, sodium methoxide, sodium hydride, sodium amide, calcium carbonate, calcium hydroxide, calcium oxide and the like or an organic base, such as, for example, a tertiary amine, e.g. N,N-diethylethanamine, N-(1-methylethyl)-2-propanamine, 4-ethyl-morpholine and the like, may be utilized to pick up the acid which is liberated during the course of the reaction.

The compounds of formula (I) wherein L is a radical of formula (b-4), said compounds being represented by (I-b-4), can also be prepared by reacting a piperidine of formula (X) with an amine of formula (XI).

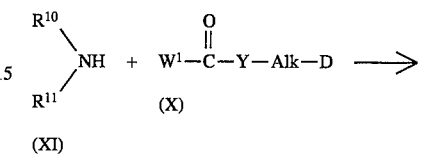

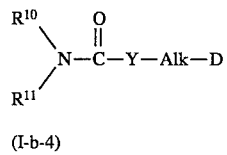

In (XI) $R^{10}$ and $R^{11}$ have the same meanings as described hereinbefore.

The compounds of formula (I) wherein L is a radical of formula (b-4) and Y is $NR^9$, said compounds being represented by (I-b-4-a), can also be prepared by reacting an amide of formula (XII) with an amine of formula (XIII).

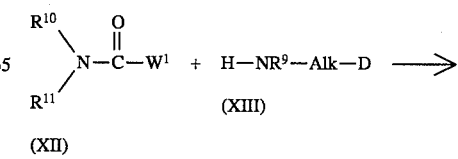

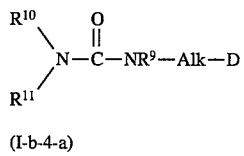

The reactions of (XI) with (X) and (XII) with (XIII) are conveniently conducted in a suitable reaction-inert solvent, such as, for example, a hydrocarbon, e.g. benzene, methylbenzene, a ketone, e.g. acetone, a halogenated hydrocarbon, e.g. dichloromethane, trichloromethane, an ether, e.g. 1,1'-oxybisethane, tetrahydrofuran and the like, a polar aprotic solvent, e.g. N,N-dimethylacetamide, N,N-dimethylformamide or a mixture of such solvents. An appropriate base such as for example, an alkali metal carbonate, sodium hydride or an organic base such as for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3) and Y is $NR^9$, said compounds being represented by formula (I-b-3-a), may also be prepared by reacting a carboxylic acid of formula (XIV) or a functional derivative with an amine of formula (XIII).

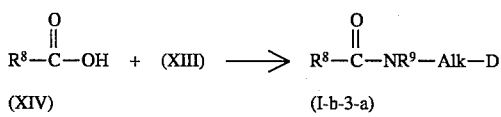

(XIV)            (I-b-3-a)

The reaction of (XIV) with (XIII) may generally be conducted following the same procedures as previously described for the amidation reaction of (V) with (IV).

The compounds of formula (I) wherein L is NC—CH$_2$—CH$_2$—, said compounds being represented by (I-c), can also be prepared by alkylating a piperidine of formula (II) with acrylonitrile (XV) in a reaction-inert solvent such as, for example, an aromatic hydrocarbon, e.g. benzene, methylbenzene and the like, an alkanol, e.g. methanol, ethanol, 2-propanol and the like, a ketone, e.g. 2-propanone and the like, an ether, e.g. tetrahydrofuran and the like, or a mixture of such solvents.

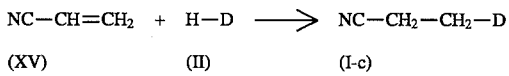

(XV)      (II)      (I-c)

The compounds of formula (I) can also be converted into each other following art-known procedures of functional group transformation. Some examples of such procedures will be cited hereinafter.

Compounds of formula (I) containing a hydroxy function may be O-alkylated according to art-known O-alkylation procedures, e.g. by stirring the former with an appropriate alkylating agent, if desired, in the presence of sodium hydride.

Compounds of formula (I) bearing a protective dioxolan ring may be deacetalized to yield the corresponding oxo compounds. Said deacetalization may be conducted following procedures widely known in the art such as, for example, by reacting the starting materials in an acidic aqueous medium.

The compounds of formula (I) containing a cyano substituent can be convened into the corresponding amines by stirring and, if desired, heating the starting cyano compounds in a hydrogen containing medium in the presence of an appropriate catalyst and such as, for example, platinum-on-charcoal, Raney nickel and the like catalysts and optionally in the presence of a base such as, for example, an amine e.g. N,N-diethylethanamine and the like, or a hydroxide, e.g. sodium hydroxide and the like. Suitable solvents are, for example, alkanols, e.g. methanol, ethanol and the like; ethers, e.g. tetrahydrofuran and the like or a mixture of such solvents.

The compounds of formula (I) may also be convened to the corresponding N-oxide-forms following art-known procedures for converting a trivalent nitrogen to its N-oxide-form. Said N-oxidation reaction may generally be carried out by reacting the starting material of formula (I) with an appropriate organic or inorganic peroxide. Appropriate inorganic peroxides comprise, for example, hydrogen peroxide, an alkali metal or earth alkali metal peroxide, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. Said N-oxidation may be carried out in a suitable solvent such as, for example, water, a lower alkanol, e.g. methanol, ethanol, propanol, butanol and the like; a hydrocarbon, e.g. benzene, methylbenzene, dimethylbenzene and the like; a ketone, e.g. 2-propanone, 2-butanone and the like, a halogenated hydrocarbon, e.g. dichloromethane, trichloromethane and the like or mixtures of such solvents. In order to enhance the reaction rate, it may be appropriate to heat the reaction mixture.

Some of the intermediates and starting materials in the foregoing preparations are known compounds while others are novel. They may be prepared according to artknown methodologies of preparing said known or similarly known compounds. Some procedures for preparing such intermediates will be described hereinafter in more detail.

The intermediates of formula (II) may be derived from an appropriately substituted piperidine of formula (XVI) by reacting the latter with a reagent of formula (V) or a functional derivative thereof, following the amidation procedures described for the preparation of (I) starting from (IV) and (V), and subsequently removing of the protective group P$^1$ in the thus obtained intermediate (XVII) following art-known procedures, e.g. by hydrolysis in an acidic or an alkaline medium or by catalytic hydrogenation, depending upon the nature of P$^1$.

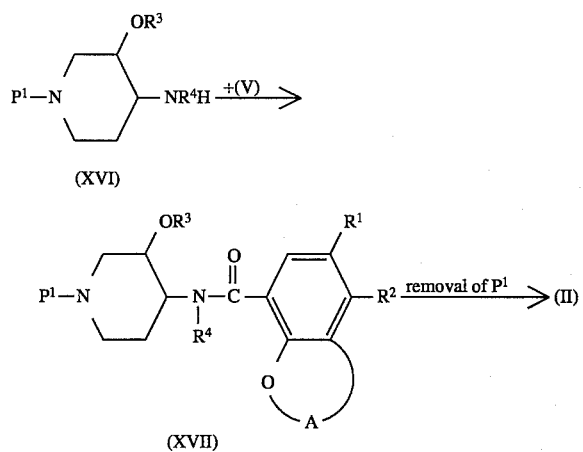

In the reaction of (XVI) with (V) and in the following reaction schemes P$^1$ represents a suitable protective group which is readily removable by hydrogenation or hydrolysis. Preferred protective groups may for example be, hydrogenolyzable groups, e.g. phenylmethyl and the like or hydrolyzable groups, such as C$_{1-4}$alkyloxycarbonyl, e.g. benzyloxycarbonyl and the like.

The intermediates of formula (IV) can be derived from an appropriately substituted piperidine of formula (XVIII) by alkylating the latter with an appropriate reagent L-W (III), following the alkylation procedures described for (I) starting from (II) and (III) and, subsequently removing the protective group P$^1$ in the thus obtained intermediate following art-known procedures described hereinbefore.

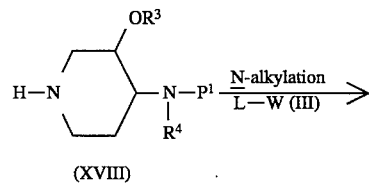

(XVIII)

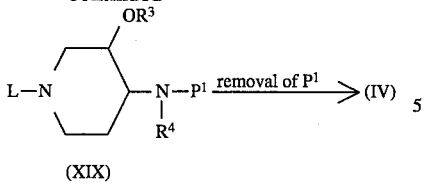

In general, the piperidines (IV), (XVI) and (XVIII) used as starting materials, can be prepared following procedures analogous to those described in Drug Development Research 8, 225–232 (1986) and in the Eur. Pat. No. 76,530 which corresponds to U.S. application Ser. No. 403,603.

The intermediates of formula (V) and the functional derivatives thereof can be prepared from an intermediate of formula (XX), wherein $W^3$ represents hydrogen or an appropriate reactive leaving group such as for example, halo, e.g. chloro, bromo, iodo and the like, by treating intermediate (XX) with an alkyl lithium, e.g. n.butyl lithium, methyl lithium and the like, an alkali metal, e.g. lithium, sodium and the like, a transition metal, e.g. magnesium, zinc, cadmium and the like or an amide, e.g. sodiumamide and the like, followed by treatment with $CO_2$ or a reagent of formula $L^1$—C(=O)—$L^1$ wherein $L^1$ represents an appropriate leaving group such as, for example, $C_{1-6}$alkyloxy, halo and the like.

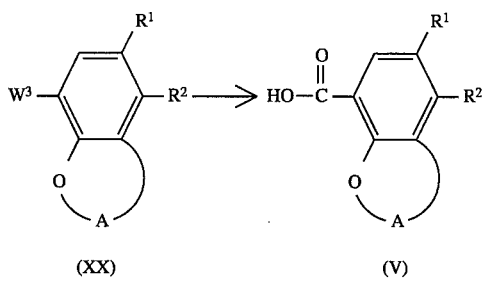

Said reaction can conveniently be carried out in a reaction-inert solvent such as for example, an aliphatic hydrocarbon, e.g. pentane, hexane, cyclohexane and the like, an aromatic solvent, e.g. benzene, chlorobenzene and the like, an ether, e.g. tetrahydrofuran, 1,4-dioxane and the like or a mixture of such solvents and optionally in the presence of an amine, e.g. ethanamine, N,N-diethylethanamine, N,N,N',N'-tetramethylethylendiamine and the like.

The intermediates of formula (XX) wherein $W^3$ is a reactive leaving group, said $W^3$ being represented by $W^{3-a}$ and said intermediates being represented by (XX-a), can in turn be obtained from (XXI) following art-known halogenation procedures optionally followed by the separation of the undesired isomers.

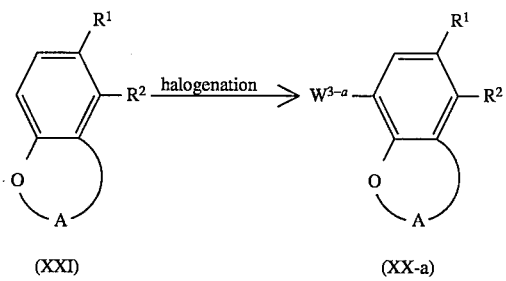

For example, an intermediate of formula (XXI) can be halogenated with a dihalide, e.g. chlorine, bromine and the like, optionally in the presence of a catalyst such as, a Lewis acid, e.g. ferric chloride, ferric bromide, aluminum chloride and the like. Intermediate (XXI) can also be halogenated with N-haloamides, e.g. N-chlorosuccinimide, N-bromosuccinimide and the like. In some instances the reaction can be catalyzed by the addition of acids, e.g. acetic acid, hydrochloric acid and the like. Said halogenation reactions can conveniently be carried out in a reaction-inert solvent such as, for example, water, an aliphatic hydrocarbon, e.g. pentane, hexane, cyclohexane and the like, an aromatic solvent, e.g. benzene, methylbenzene and the like, a halogenated hydrocarbon, e.g. dichloromethane, tetrachloromethane and the like, or an ether, e.g. 1,1'-oxybisethane, tetrahydrofuran and the like.

The intermediates of formula (XXI) wherein $R^1$ is other than hydrogen, said $R^1$ being represented by $R^{1-a}$ and said intermediates by (XXI-a), can be prepared by halogenation or sulfonylation of an intermediate of formula (XXII).

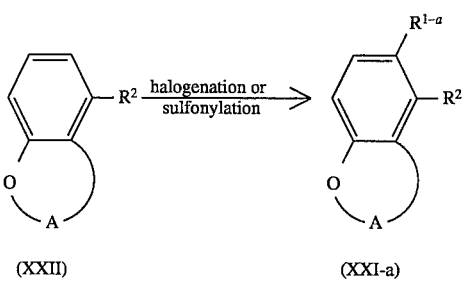

The halogenation reaction can be carried out according to the halogenation procedures described hereinbefore for the halogenation of (XXI). The sulfonylation reaction can be carried out by treating intermediate (XXII) with, for example, a sulfonyl halide, e.g. $C_{1-6}$alkylsulfonyl chloride, $C_{1-6}$alkylsulfonyl bromide and the like, optionally in the presence of a catalyst such as, a Lewis acid, e.g. ferric chloride, ferric bromide, aluminum chloride and the like; or by halosulfonation with chlorosulfuric acid followed by treatment with ammonia.

The starting materials of formula (XXII) wherein A is —$CH_2$—$CH_2$—, —$CH_2$—$CH_2$—$CH_2$—, or —$CH_2$—$CH_2$—$CH_2$—$CH_2$—, wherein one or two hydrogen atoms may be replaced by $C_{1-6}$alkyl, said A being represented by $A^1$, and said intermediates by formula (XXII-a), can be obtained by cyclizing an intermediate of formula (XXIII) in the presence of an acid such as, for example, hydrochloric acid, hydrobromic acid and the like, or mixtures thereof with acetic acid.

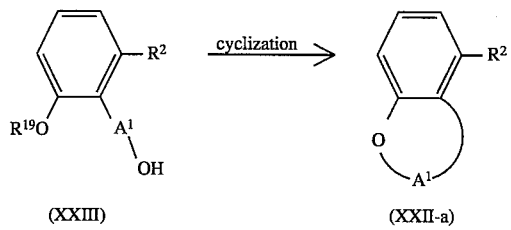

In intermediate (XXIII) and throughout the following description and reaction schemes $R^{19}$ is $C_{1-4}$alkyl.

The intermediates of formula (XXIII), in turn, can be prepared by deprotecting the functionalized alcohol in intermediate (XXIV).

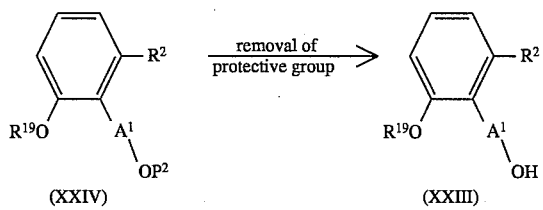

In formula (XXIV) $P^2$ is a protective group such as for example, tetrahydropyranyl, tertiair butyl, phenylmethyl and the like. These protective groups are readily removable by hydrolysis with for example, an acid, e.g. hydrochloric acid, hydrobromic acid, acetic acid and the like or by catalytic hydrogenation in the presence of hydrogen and an appropriate catalyst. In case $R^2$ is amino, it may be expedient to protect this group during the course of the above and the following reactions to avoid undesired side reactions. Suitable protective groups are, for example, $C_{1-6}$alkylcarbonyl, $C_{1-6}$alkyloxycarbonyl, benzyloxycarbonyl and arylmethyl groups. The removal of the protective group may generally be carried out by deblocking, for example, a $C_{1-6}$alkylcarbonyl group with an appropriate acid or base in an anhydric or aqueous organic solvent or in water, or by catalytic hydrogenation in the presence of hydrogen and an appropriate catalyst depending upon the nature of the protective group.

The intermediates of formula (XXIV) can be obtained by reduction of an intermediate of formula (XXV).

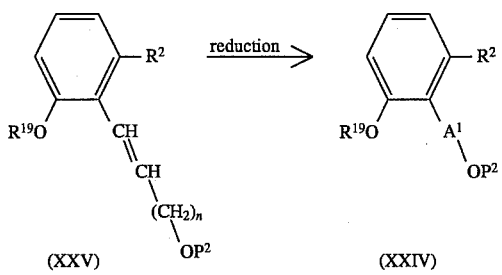

It is to be understood that in formula (XXV) and the subsequent formulae one or two hydrogen atoms of the carbon chain may be replaced by a $C_{1-6}$alkyl radical, and n can be 0, 1 or 2. The double bond of formula (XXV) may be reduced by catalytic hydrogenation in a suitable solvent, e.g. methanol or ethanol and the like in the presence of hydrogen and an appropriate catalyst e.g. platinum-on-charcoal, palladium-on-charcoal, Raney nickel and the like, optionally at an increased temperature and/or pressure.

The intermediates of formula (XXV) can be prepared by reacting an aldehyde (XXVI) with a suitable ylide such as, for example, a phosphorus ylide (e.g. $R^{20}$ and $R^{21}$ are aryl or alkyl: Wittig reaction) or an ylide prepared from a phosphonate (e.g. $R^{20}$ is alkyloxy and $R^{21}$ is $O^-$: Horner-Emmons reaction).

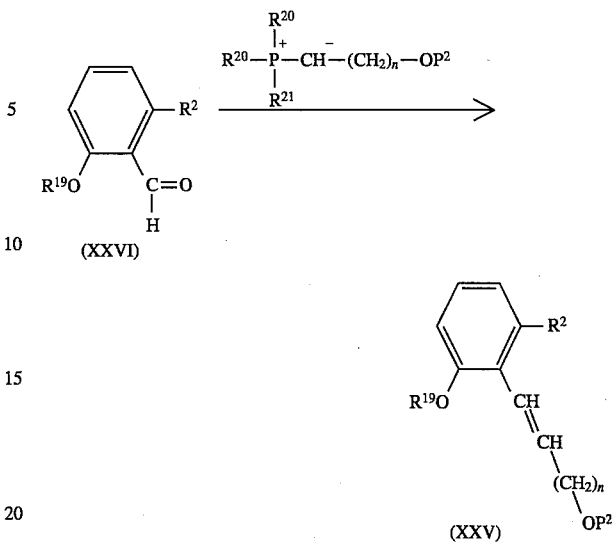

Said ylide can be obtained by treating a phosphonium salt or a phosphonate with an appropriate base such as, for example, potassium tert.butoxide, n.butyl lithium, sodium amide, sodium hydride and the like bases under an inert atmosphere and in a reactioninert solvent such as, for example, an ether, e.g. tetrahydrofuran, 1,4-dioxane and the like.

The intermediates of formula (XXVI) can conveniently be obtained from an alkyloxybenzene derivative of formula (XXVII) following art-known formylation procedures, optionally followed by the separation of the undesired isomers.

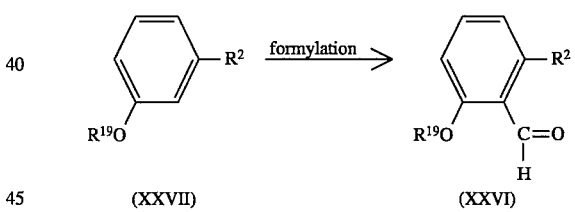

For example, the alkyloxybenzene derivative of formula (XXVII) can be formylated by reaction with an appropriate base such as, for example, an alkyl lithium, e.g. methyl lithium, n.butyl lithium, and the like, and subsequently reacting the thus obtained metalated alkyloxybenzene derivative with a formamide, e.g. N,N-dimethylformamide, N-methyl-N-phenylformamide, and the like. Said formylation may also be conducted under Vilsmeier-Haack (phosphoryl chloride, formamide) or Gattermann (zinc(II)cyanide, hydrochloric acid) conditions in an acidic medium.

Alternatively, the starting intermediates of formula (XXII), wherein A is —$CH_2$—$CH_2$—, wherein one or two hydrogen atoms may be replaced by $C_{1-6}$alkyl, said intermediates being represent by formula (XXII-a-1), can be obtained by cyclizing an intermediate of formula (XXIII-a-1) in an acidic medium according to the procedures described in J. Het. Chem., 17, 1333 (1980).

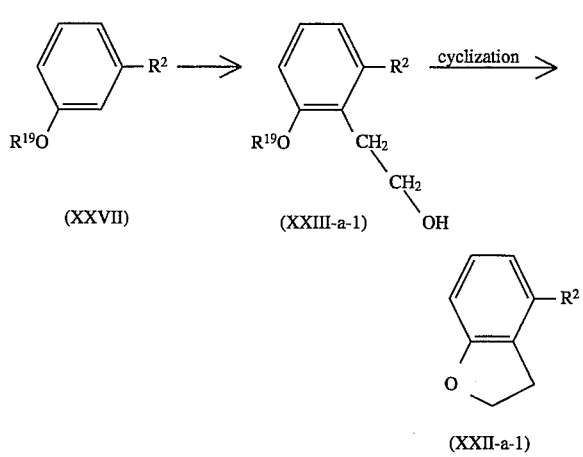

It is to be understood that in formula (XXII-a-1) and (XXII-a-1) one or two hydrogen atoms of the ethyl or tetrahydrofuran moiety may be replaced by a $C_{1-6}$alkyl radical. The desired intermediates of formula (XXII-a-1) can be obtained from an alkyloxybenzene derivative of formula (XXVII) by reaction the latter with an ethylene oxide derivative in a reaction inert solvent such as, for example, an ether, e.g. tetrahydrofuran, 1,4-dioxane, and the like in the presence of a base. Appropriate bases are, for example, alkyl lithium, e.g. methyl lithium, n.butyl lithium and the like.

The starting intermediates of formula (XXII), wherein $R^2$ is amino and A is —$CH_2$—$CH_2$—O—, wherein one or two hydrogen atoms may be replaced by $C_{1-6}$alkyl, said intermediates being represented by formula (XXII-a-5), can be obtained by reduction of the azide group of formula (XXVIII) to the corresponding amino group.

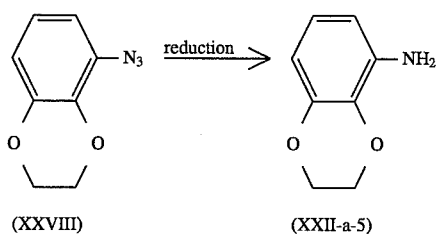

Said reduction reaction can be carried out with an appropriate reductant such as, for example, lithium aluminum hydride or 1,2-ethanedithiol in a reaction-inert solvent. It is to be understood that in formula (XXII-a-5) and the subsequent formulae (XXVIII), (XXIX) and (XXX) one or two hydrogen atoms of the dioxine moiety may be replaced by a $C_{1-6}$alkyl radical.

The above intermediates of formula (XXVIII) can be prepared, in two steps, by lithiation of dihydrobenzodioxin of formula (XXX) with an alkyl lithium, e.g. n.butyl lithium and the like, followed by a treatment with sodium azide.

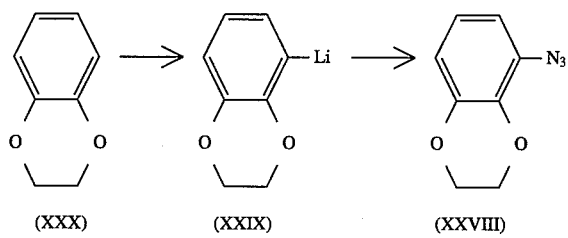

The starting intermediates of formula (XXII), wherein $R^2$ is amino and A is —$CH_2$—$CH_2$—$CH_2$—O—, wherein one or two hydrogen atoms may be replaced by $C_{1-6}$alkyl, said intermediates being represented by formula (XXII-a-6), can be prepared by a cycloalkylation reaction of 3-nitrocatechol (XXXI) with 1,3-dibromopropane (XXXII) according to the procedures described in J. Med. Chem., 31, 1934 (1988). Subsequent reduction of the nitro-group of formula (XXXIII) following art-known nitro-to-amino reduction procedures provide the aniline derivative (XXII-a-6).

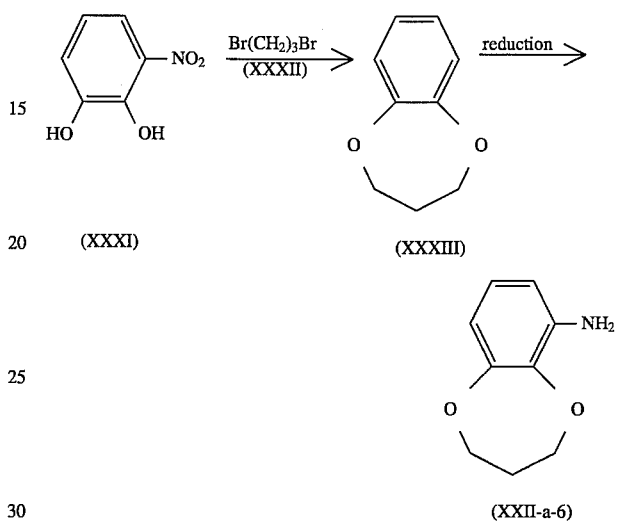

It is to be understood that in formula (XXII-a-6), (XXXII) and (XXXIII), one or two hydrogen atoms of the alkyl or dioxepin moiety may be replaced by a $C_{1-6}$alkyl radical.

The starting materials of formula (XXI), wherein $R^1$ is chloro, $R^2$ is amino and A is —$CH_2$—$CH_2$—O—, said intermediates being represented by (XXl-a-5), can be prepared as described in J. Chem. Soc., 1315 (1955), by reduction of the corresponding nitro-derivative of formula (XXXIV), following art-known nitro-to-amino reduction procedures such as, for example, catalytic hydrogenation in a suitable solvent in the presence of hydrogen and an appropriate catalyst, e.g. platinum-on-charcoal and the like. The nitrobenzodioxin derivative (XXXIV) can in turn be obtained by diazotation of the aminodinitrobenzodioxin derivative of formula (XXXV), dediazonation and nucleophilic aromatic substitution with chloride.

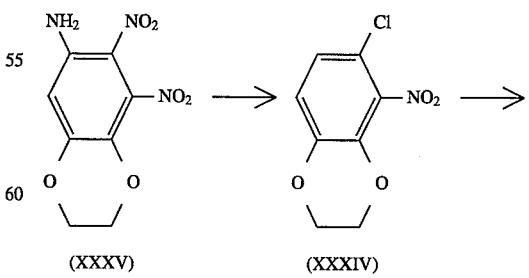

-continued

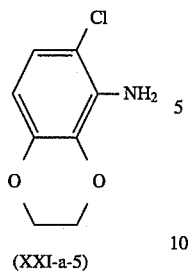

(XXI-a-5)

It is to be understood that in formula (XXI-a-5) and the subsequent formulae (XXXIV) and (XXXV) one or two hydrogen atoms of the dioxin moiety may be replaced by a $C_{1-6}$alkyl radical.

The basic intermediates of formula (V) can also be prepared by hydrolyzing the ester group of formula (XXXVI) in a basic or acidic aqueous medium.

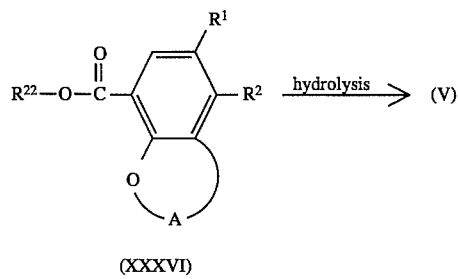

(XXXVI)

In (XXXVI) and throughout the following description and reaction schemes $R^{22}$ is a $C_{1-4}$alkyl radical.

The above esters of formula (XXXVI) in turn can be obtained by halogenation or sulfonylation of the intermediates of formula (XXXVII) according to the procedures described hereinbefore for the preparation of the intermediates of formula (XXI-a) from (XXII).

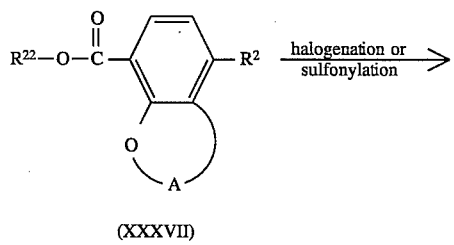

(XXXVII)

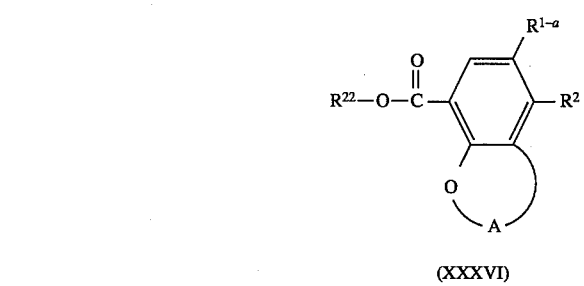

(XXXVI)

The intermediates of formula (XXXVII), wherein A is —C(CH$_3$)$_2$—CH$_2$—, said intermediates being represented by formula (XXXVII-a-1) can be obtained by cyclizing the phenyl allyl intermediate (XXXVIII), in the presence of an acid, for example, formic acid, acetic acid, hydrogen bromide and the like, or a mixture of these acids.

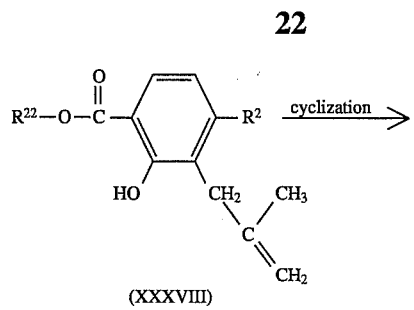

(XXXVIII)

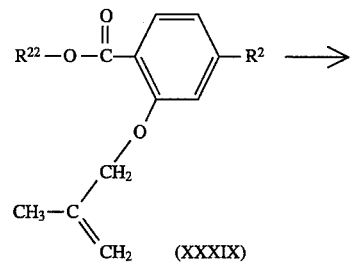

(XXXVII-a-1)

The above phenyl allyl intermediate (XXXVIII) can be prepared by a Claisen rearrangment of a phenyl allyl ether of formula (XXXIX).

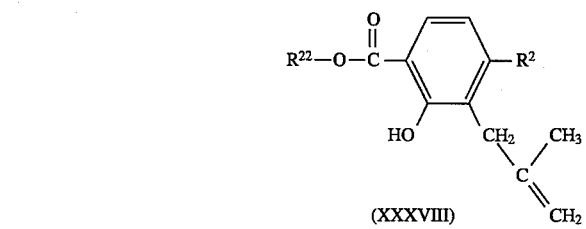

(XXXIX)

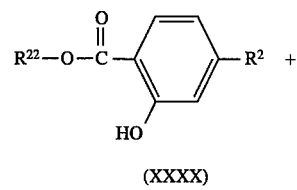

(XXXVIII)

Said reaction can be carried out in a reaction-inert solvent at a somewhat elevated temperature, in particular the reflux temperature of the reaction mixture. Suitable solvents are, for example, aliphatic or aromatic hydrocarbons, e.g. methylbenzene, phenylbenzene and the like, halogenated hydrocarbons, e.g. chlorobenzene and the like, alcohols, e.g. cyclohexanol anti the like, ethers, e.g. 1,1'-oxybisethane, 1,1'-oxybisbenzene and the like, amines, e.g. N,N-dimethylaniline and the like; dipolar aprotic solvents, e.g. N,N-dimethylformamide, 1-methyl-2-pyrrolidinone and the like.

The phenyl allyl ether of formula (XXXIX) can in turn be prepared by the O-alkylation reaction of a phenol intermediate of formula (XXXX) with an alkylating reagent of formula (XXXXI) following art-known O-alkylation procedures.

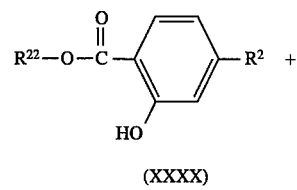 +

(XXXX)

-continued

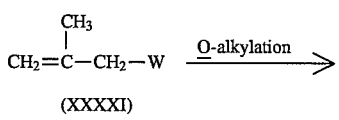
(XXXXI)

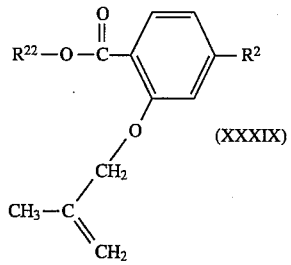
(XXXIX)

In formula (XXXXI) W is defined as described hereinbefore for intermediate (III). Said O-alkylation reaction can conveniently be carried out by mixing the reactants, optionally in a reaction-inert solvent such as, for example, water, an aromatic solvent, e.g. benzene and the like, a $C_{1-6}$alkanol, e.g. ethanol and the like, a ketone, e.g. 2-propanone and the like, an ether, e.g. tetrahydrofuran and the like, or a dipolar aprotic solvent, e.g. N,N-dimethylformamide and the like. The addition of an appropriate solvent compatible base such as, for example potassium carbonate, sodium hydroxide or sodium hydride and the like may optionally be used to pick up the acid which is formed during the course of the reaction.

The intermediates of formula (XXXVI), wherein A is —$CH_2$—$CH_2$—$CH_2$— wherein one or two hydrogen atoms may be replaced by $C_{1-6}$alkyl, said intermediate being represented by formula (XXXVI-a-2), can be obtained by reduction of a 2H-benzopyran of formula (XXXXII) following the reduction procedures described hereinbefore for the preparation of the intermediates of formula (XXIV).

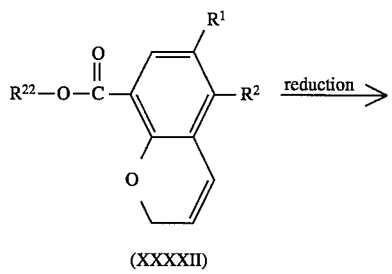
(XXXXII)

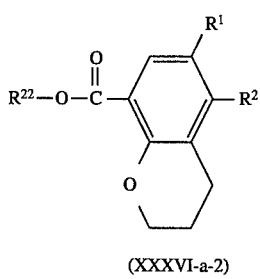
(XXXVI-a-2)

It is to be understood that in formula (XXXVI-a-2), (XXXXII) and (XXXIII) one or two hydrogen atoms of the pyran moiety or carbon chain may be replaced by $C_{1-6}$alkyl.

The intermediates of formula (XXXXII) can be prepared by a Claisen rearrangement of the phenylether of formula (XXXXIII) followed by a cyclization reaction to obtain the intermediate of formula (XXXXII).

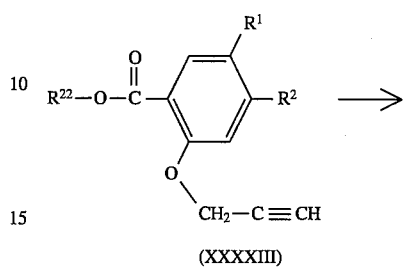
(XXXXIII)

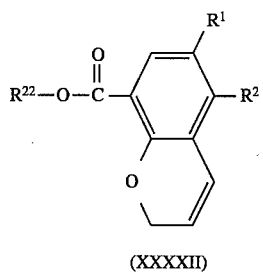
(XXXXII)

Said reaction can be carried out according to similar reacting procedures as described in Elderfield, Heterocyclic Compounds, Vol. 2, pages 393–418. Preferably the rearrangment is carried out in a reaction-inert solvent at temperatures above 100° C. Suitable solvents are for example, hydrocarbons, e.g. phenylbenzene, diphenylmethane, naphthalene, decahydronaphthalene and the like, halogenated hydrocarbons, e.g. chlorobenzene and the like, alcohols, e.g. cyclohexanol and the like, ethers; e.g. 1,1'-oxybisbenzene and the like.

In some instances the Claisen rearrangement of the phenylether of formula (XXXXIII) results in a benzofuran of formula (XXXXIV) instead of a 2H-benzopyran of formula (XXXXII). A benzofuran of formula (XXXXIV) is obtained when the Claisen rearrangement reaction is carded out in the presence of an appropriate base such as for example, an alkali metal or an earth alkaline metal carbonate, hydrogen carbonate, hydroxide and the like, or in an appropriate solvent such as for example, an amine, e.g. pyridine, quinoline, N,N-diethylbenzenamine and the like, a dipolar aprotic solvent, e.g. N,N-dimethylfomamide, N,N-dimethylacetamide, and the like.

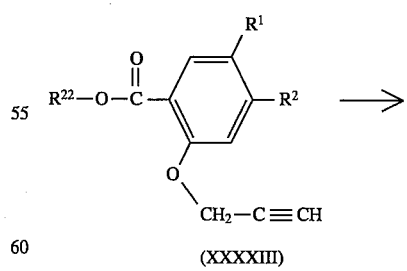
(XXXXIII)

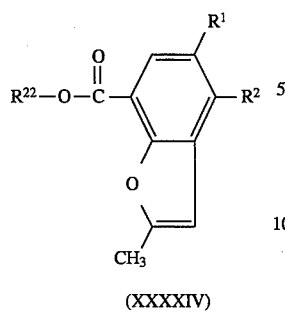

(XXXXIV)

The intermediates of formula (II) and (XVII) wherein $R^1$, $R^2$, $R^3$, $R^4$, A and $P^1$ have the above described meanings are deemed to be novel, and as such they represent an additional feature of the present invention. In addition the intermediates of formula (V) and (XXXVI) wherein $R^1$ is chloro and $R^2$ is amino are believed to be novel compounds and constitute a further aspect of the invention.

Pure stereochemically isomeric forms of the compounds of formula (I) and the intermediates of formula (II) may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids or their optically activated derivatives.

It is evident that the cis and trans diastereomeric racemates may be further resolved into their optical isomers, cis(+), cis(−), trans(+) and trans(−) by the application of methodologies known to those skilled in the art.

Pure stereochemically isomeric forms may also be derived from the corresponding pure stereochemically isomeric forms of the appropriate starting materials, provided that the reaction occurs stereospecifically.

The compounds of formula (I) containing an alkene moiety may be present in a "E" or "Z" form, said E- and Z-notation having the meanings described in J. Org. Chem., 35, 2849–2868 (1970).

The compounds of formula (I) and the intermediates of formula (II), the N-oxide forms, the pharmaceutically acceptable salts and possible stereoisomeric forms thereof possess favourable gastrointestinal motility stimulating properties. In particular the present compounds show significant motility enhancing effects on the colon. The latter property is clearly evidenced by the results obtained in the "colon ascendents induced contractions" test described hereinafter.

The stimulatory effect of the subject compounds of formula (I) and (II) on the motility of the gastrointestinal system may further be evidenced by, for example, the various test models described in The Journal of Pharmacology and Experimental Therapeutics, 234, 775–783 (1985) and in Drug Development Research 8, 243–250 (1986). The "Gastric emptying of a liquid meal in rats" test described in the latter article and the "Gastric emptying of an acaloric meal in conscious dog after administration of lidamidine" test. further revealed that a representative number of compounds also significantly accelerated gastric emptying.

In addition, the present compounds of formula (I) and (II), the N-oxide forms, the pharmaceutically acceptable acid addition salts and possible stereoisomeric forms thereof have a particular receptor binding profile. Some groups of compounds within the present invention, particularly those wherein the radical A is not substituted with $C_{1-6}$alkyl have a poor $5HT_3$ antagonistic activity as induced by high doses of serotonin on the guinea pig ileum. The most compounds of the invention do not show any apparent marked receptor-binding affinity with serotonergic-$5HT_1$ and serotonergic-$5HT_2$ receptors and have little or no dopaminergic antagonistic activity.

In view of their useful gastrointestinal motility enhancing properties the subject compounds may be formulated into various forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the gastrointestinal system and, in particular their capacity to enhance the motility of the colon, the subject compounds are useful to normalize or to improve the gastric and intestinal emptying in subjects suffering from a disturbed motility, e.g. a decreased peristalsis of the stomach and/or of the small and/or large intestine.

In view of the utility of the compounds of the present invention, there is provided a method of treating warm-blooded animals suffering from motility disorders of the gastrointestinal system such as, for example, gastroparesis, flatulent dyspepsia, nonulcer dyspepsia, pseudo-obstruction, and in particular impaired colonic transit. Said method comprises the systemic administration of an effective gastrointestinal motorstimulating amount of a compound of formula (I), a N-oxide, a pharmaceutically acceptable acid addition salt or a possible stereoisomeric form thereof, to warm-blooded animals. Some particular compounds of the invention also posses therapeutic value in the treatment of upper bowel motility and gastroesophageal reflux disorders.

Those of skill in the pertinent art could easily determine the effective motorstimulating amount from the test results presented hereinafter. In general it is contemplated that an effective amount would be from 0.001 mg/kg to 10 mg/kg body weight, and more preferably from 0.01 mg/kg to 1 mg/kg body weight. The following examples are intended to illustrate and not to limit the invention in all its aspects. Unless otherwise stated all parts therein are by weight.

Experimental Part

A. Preparation of the intermediates

EXAMPLE 1 a) To a solution of 8.1 parts of 4-amino-5-chloro-2,3-dihydro-2,2-dimethyl-7-benzofurancarboxylic acid in 218 parts of trichloromethane and 3.43 parts of N,N-diethylethanmine were added dropwise 3.63 parts of ethyl chloroformate, keeping the temperature below 10° C. After stirring for ½ hour at 10° C., the whole was added to a solution of 6.26 parts of ethyl 4-amino-3-methoxy-1-piperidinecarboxylate in 145 parts of trichloromethane at 10° C. Stirring was continued for ½ hour at room temperature. The reaction mixture was washed with water, NaOH 5% and water and was then dried, filtered and evaporated. The residue was suspended in 2,2'-oxybispropane. The product was filtered off and dried, yielding 12.3 parts (93.2%) of ethyl cis-4-[(4-amino-5-chloro-2,3-dihydro-2,2-dimethyl-7-benzofuranyl)-carbonylamino]-3-methoxy-1-piperidinecarboxylate (interm. 1).

b) A mixture of 12.3 parts of intermediate 1, 15.9 parts of potassium hydroxide and 156 parts of 2-propanol was stirred for 12 hours at reflux temperature. The reaction mixture was evaporated and water was added to the residue. The whole was evaporated again and the residue was diluted with water. The product was extracted with dichloromethane (2×) and the combined extracts were dried, filtered and evaporated. The residue was purified by column chromatography (silica gel; $CH_2Cl_2/CH_3OH(NH_3)$ 90:10). The eluent of the desired fraction was evaporated and the residue was suspended in 2,2'-oxybispropane. The product was filtered off and dried, yielding 7.24 parts (71.0%) of cis-4-amino-5-chloro-2,3-dihydro-N-(3-methoxy-4-piperidinyl)-2,2-dimethyl-7-benzofurancarboxamide; mp. 179.3° C. (interm. 5).

In a similar manner there were also prepared the intermediates listed in Table 1.

TABLE 1

[Structure: HN-piperidine with OR³ substituent —NH—C(=O)— aryl with Cl, NH₂ and —O—A— fused ring]

| Int. No. | R³ | —O—A— | mp.(°C.) |
|---|---|---|---|
| 2* | —CH₃ | —O—(CH₂)₂— | 210.9 |
| 3 | —H | —O—(CH₂)₂— | 260.4 |
| 4 | —CH₃ | —O—(CH₂)₂—O— | — |
| 5 | —CH₃ | —O—C(CH₃)₂—CH₂— | 179.3 |
| 6 | —CH₃ | —O—CH(CH₃)—CH₂— | 199.7 |
| 7 | —CH₃ | —O—(CH₂)₃— | 225.2 |

*note: for intermediate no. 2, no water was added to the residue.

EXAMPLE 2 a) A solution of 9.1 parts of 5-chloro-2,3-dihydro-4-benzofuranamine [described in J. Het. Chem., 17(6) 1333 (1980)], 9.6 parts of N-bromosuccinimide and 130.5 parts of benzene was stirred for 1 hour at reflux temperature. The solvent was evaporated and the residue was dissolved in 387.4 parts of trichloromethane. The solution was washed with water (2×200 parts). The organic layer was dried, filtered and evaporated. The residue was purified by column chromatography (silica gel; $C_6H_{14}/CH_2Cl_2$ 50:50). The eluent of the desired fraction was evaporated, yielding 11.8 parts (87.9%) of 7-bromo-5-chloro-2,3-dihydro-4-benzofuranamine (interm. 8).

b) To a cooled (−70° C.) and stirred mixture of 15.6 parts of a solution of n.butyllithium in hexane 2.5M and 44.5 parts of tetrahydrofuran was added dropwise a solution of 4 parts of intermediate 8 in 26.7 parts of tetrahydrofuran under a nitrogen flow. The reaction mixture was stirred for 1 hour at about −60° C. and was poured into a saturated suspension of carbondioxide (ice) in 44.5 parts of tetrahydrofuran. The whole was allowed to warm up to room temperature while being stirred and 80 parts of water were added. The aqueous layer was neutralized with hydrochloric acid and the formed precipitate was filtered off and dried in vacuo at 60° C. yielding 1.1 parts (32.2%) of 4-amino-5-chloro-2,3-dihydro-7-benzofurancarboxylic acid; mp. 258.4° C. (interm. 9). In a similar manner there was also prepared: 8-amino-7-chloro-2,3-dihydro-1,4-benzodioxin-5-carboxylic acid (interm. 10).

EXAMPLE 3 a) A mixture of 40 parts of methyl 4-(acetylamino)-5-chloro-2-(2-propynoxy)benzoate and 172 parts of phenoxybenzene was stirred for 45 min. at 230° C. After cooling, the reaction mixture was poured into petroleumether. The organic layer was separated, dried, filtered and evaporated. The residue was purified by column chromatography (silica gel; $CH_2Cl_2/CH_3OH$ 97:3), The eluent of the desired fractions was evaporated and the residue was crystallized from acetonitrile, yielding 11.9 parts (33.8%) of methyl 5-(acetylamino)-6-chloro-2H-1-benzopyran-8-carboxylate (interm. 11).

b) A mixture of 31.3 parts of intermediate 11, 31 parts of N,N-diethylethanamine and 395 parts of methanol was hydrogenated at normal pressure and room temperature with 4 parts of palladium-on-charcoal catalyst 10%. After the calculated amount of hydrogen was taken up, the catalyst was filtered off and the filtrate was evaporated. The residue was suspended in water and the product was extracted with dichloromethane (2×). The combined extracts were washed with water, dried, filtered and evaporated. The residue was purified twice by column chromatography (silica gel; CH$_2$Cl$_2$/CH$_3$OH 97.5:2.5). The eluent of the desired fraction was evaporated and the residue was crystallized from acetonitrile. The product was filtered off and dried, yielding 19.1 parts (69.7%) of methyl 5-(acetylamino)-3,4-dihydro-2H-1-benzopyran-8-carboxylate; mp. 175.1 ° C. (interm. 12).

c) A mixture of 19.1 parts of intermediate 12, 10.22 parts of N-chlorosuccinimide and 237 parts of acetonitrile was stirred for 1 hour at reflux temperature. After cooling, the reaction mixture was poured into 300 parts of water. The product was extracted with dichloromethane (2×) and the combined extracts were washed with water, dried, filtered and evaporated. The residue was suspended in 2,2'-oxybispropane. The product was filtered off and dried, yielding 17.8 parts (81.5%) of methyl 5-(acetylamino)-6-chloro-3,4-dihydro-2H-1-benzopyran-8-carboxylate; mp. 184.2° C. (interm. 13).

d) A mixture of 1.34 parts of intermediate 13, 2.62 parts of potassium hydroxide and 20 parts of water was stirred for 3 hours at reflux temperature. After cooling, the reaction mixture was acidified to pH 4 with concentrated hydrochloric acid. The precipitate was filtered off and dried, yielding 0.65 parts (60.7%) of 5-amino-6-chloro-3,4-dihydro-2H-1-benzopyran-8-carboxylic acid; mp. 225.9° C. (interm. 14).

EXAMPLE 4 a) To a solution of 104.6 parts of methyl 2-hydroxy-4-(acetylamino)benzoate in 470 parts of N,N-dimethylformamide were added portionwise 24 parts of a dispersion of sodium hydride in mineral oil (50%) under a nitrogen atmosphere. After stirring for 1 hour at room temperature, there was added a solution of 55.2 parts of 3-chloro-2-methyl-1-propene in 47 parts of N,N-dimethylformamide. Stirring was continued for 3 days at 50° C. The reaction mixture was evaporated and the residue was dissolved in dichloromethane. This solution was washed with water, sodium hydroxide 10% and water and was then dried, filtered and evaporated. The residue was crystallized from 2,2'-oxybispropane. The product was filtered off and dried, yielding 65.8 parts (50.0%) of methyl 4-(acetylamino)-2-[(2-methyl-2-propenyl)oxy]benzoate (interm. 15).

b) A mixture of 72 parts of intermediate 15 and 226 parts of 1-methyl-2-pyrrolidinone was stirred for 1.5 hour at reflux temperature. After cooling, the reaction mixture was poured into ice-water. The product was extracted with dichloromethane (2×) and the combined extracts were washed with water, dried, filtered and evaporated. The residue was crystallized from 2,2-oxybispropane. The product was filtered off and dried, yielding 35.4 parts (49.8%) of methyl 4-(acetylamino)-2-hydroxy-3-(2-methyl-2-propenyl)benzoate. The mother liquor was evaporated and the residue was successively suspended in water and recrystallized from 2,2'-oxybispropane, yielding an additional 17.6 parts (24.8%) of methyl 4-(acetylamino)-2-hydroxy-3-(2-methyl-2-propenyl)benzoate. Total yield: 53.0parts (74.6%) (interm. 16).

c) A mixture of 126 parts of intermediate 16 and 1220 parts of formic acid was stirred for 20 hours at reflux temperature. After cooling, the reaction mixture was poured into ice-water and the whole was extracted with dichloromethane (2×). The combined extracts were washed with sodium hydroxide 10% and water and were then dried, filtered and evaporated. The residue was suspended in 2,2'-oxybispropane. The product was filtered off and dried, yielding 105.5 parts (83.8%) of methyl 4-(acetylamino)-2,3-dihydro-2,2-dimethyl-7-benzofurancarboxylate (interm. 17).

d) A mixture of 10.5 parts of intermediate 17, 5.87 parts of N-chlorosuccinimide and 158 parts of acetonitrile was stirred for 1 hour at reflux temperature. After cooling, the reaction mixture was poured into ice-water. The product was extracted with dichloromethane (2×) and the combined extracts were dried, filtered and evaporated. The residue was suspended in 2,2'-oxybispropane. The product was filtered off and dried, yielding 11.9 parts (99.9%) of methyl 4-(acetylamino)-5-chloro-2,3-dihydro-2,2-dimethyl-7-benzofurancarboxylate (interm. 18).

e) A mixture of 11.9 parts of intermediate 18, 22.4 parts of potassium hydroxide and 200 parts of water was stirred for 3 hours at reflux temperature. After cooling, the reaction mixture was acidified to pH 4–5. The precipitate was filtered off and dried, yielding 8.1 parts (83.8%) of 4-amino-5-chloro-2,3-dihydro-2,2-dimethyl-7-benzofurancarboxylic acid (interm. 19).

B. Preparation of the final compounds

EXAMPLE 5

A mixture of 3.9 parts of intermediate 2, 2.54 parts of sodium carbonate, one crystal of potassium iodide and 144 parts of 4-methyl-2-pentanone was stirred for 1 hour at reflux temperature using a water separator. After the addition of 3.2 parts of 1-(2-chloroethyl)-3-ethyl-2,3-dihydro-1H-benzimidazol-2-one, stirring was continued overnight at reflux temperature. The reaction mixture was washed with water. The organic layer was dried, filtered and evaporated. The residue was purified by column chromatography (silica gel; CH$_2$Cl$_2$/CH$_3$OH 96:4). The eluent of the desired fraction was evaporated and the residue was crystallized from 2,2'-oxybispropane. The product was dried in vacuo at 70° C., yielding 2.30 parts (37.3%) of cis-4-amino-5-chloro-N-[1-[2-(3-ethyl-2,3-dihydro-2-oxo-1H-benzimidazol-1-yl)-ethyl]-3-methoxy-4-piperidinyl]-2,3-dihydro-7-benzofurancarboxamide mp. 173.7° C. (comp. 1).

EXAMPLE 6

A mixture of 4.2 parts of 3-(2-bromoethyl)-2-methyl-4H-quinazolin-4-one monohydrobromide, 3.3 parts of intermediate 2, 4.24 parts of sodium carbonate, 160 parts of 4-methyl-2-pentanone and a few crystals of potassium iodide was stirred for 20 hours at reflux temperature. The solvent was evaporated and the residue was partitioned between trichloromethane and water. The organic layer was washed with water, dried, filtered and evaporated. The residue was purified twice by column chromatography (silica gel; CHCl$_3$/CH$_3$OH 97:3; HPLC; silicagel; C$_6$H$_5$-CH$_3$/i. C$_3$H$_7$OH 80:20). The eluent of the desired fraction was evaporated and the residue was crystallized from acetonitrile. The product was filtered off and dried in vacuo at 60° C., yielding 3.10 parts (60.5%) of cis-4-amino-5-chloro-2,3-dihydro-N-[3-methoxy-1-[2-(2-methyl-4-oxo-3(4H)-quinazolinyl)-ethyl]-4-piperidinyl]-7-benzofurancarboxamide; mp. 274.9° C. (comp. 30).

EXAMPLE 7

A mixture of 4.07 parts of intermediate 7, 3.82 parts of sodium carbonate and 200 parts of 4-methyl-2-pentanone was stirred and refluxed (with water separation) for 1 hour. There were added 2.7 parts of 6-chloro-2-(3-chloropropyl)-2H-pyridazin-3-one and stirring at reflux temperature was continued overnight. The reaction mixture was evaporated and the residue was taken up in dichloromethane. This solution was washed with water, dried, filtered and evaporated. The residue was purified by column chromatography (silica gel; $CH_2Cl_2/CH_3OH(NH_3)$ 95:5). The eluent of the desired fraction was evaporated and the residue was solidified in 2,2'-oxybispropane. The product was filtered off and dried, yielding 3.9 parts (63.7%) of cis-5-amino-6-chloro-N-[1-[3-(3-chloro-1,6-dihydro-6-oxo-1-pyridazinyl)propyl]-3-methoxy-4-piperidinyl]-3,4-dihydro-2H-benzopyran-8-carboxamide; mp. 149.5° C. (comp. 136).

EXAMPLE 8

A mixture of 3.4 parts of intermediate 7, 3.16 parts of tetrahydro-2-furanmethanol methanesulfonate (ester), 80 parts of 4-methyl-2-pentanone and, 1.58 parts of sodium carbonate was stirred and refluxed (with water separation) for 30 hours. The reaction mixture was evaporated and the residue was diluted with water. The product was extracted with dichloromethane (2×) and the combined extracts were washed with water, dried, filtered and evaporated. The residue was purified by column chromatography (silica gel; $CH_2Cl_2/CH_3OH$ 95:5). The eluent of the desired fraction was evaporated and the residue was suspended in 2,2'-oxybispropane. The product was filtered off and dried, yielding 2.44 parts (57.6%) of cis-5-amino-6-chloro-3,4-dihydro-N-[3-methoxy-1-[(tetrahydro-2-furanyl)methyl]-4-piperidinyl]-2H-1-benzopyran-8-carboxamide; mp. 158.1° C. (comp. 76).

EXAMPLE 9

A mixture of 3.53 parts of intermediate 5, 2.1 parts of 1-(3-chloropropyl)-3-ethyl-2-imidazolidinone, 94 parts of N,N-dimethylformamide and 1.58 parts of sodium carbonate was stirred for 20 hours at 70° C. The reaction mixture was evaporated and the residue was diluted with water. The product was extracted with dichloromethane (2×) and the combined extracts were washed with water, dried, filtered and evaporated. The residue was purified by column chromatography (silica gel; $CH_2Cl_2/CH_3OH(NH_3)$ 96:4). The eluent of the desired fraction was evaporated and the residue was converted into the ethanedioate salt in 2-propanol. The product was filtered off and dried, yielding 4.18 parts (70.0%) of cis-4-amino-5-chloro-N-[1-[3-(3-ethyl-2-oxo-1-imidazolidinyl)-propyl]-3-methoxy-4-piperidinyl]-2, 3-dihydro-2,2-dimethyl-7-benzofurancarboxamide ethanedioate(1:1); mp. 208.0° C. (comp. 121).

EXAMPLE 10

A mixture of 2.6 parts of 2-iodomethyl-1,3-dioxolane, 3.3 parts of intermediate 2, 2.12 parts of sodium carbonate and 47 parts of N,N-dimethylformamide was stirred for 3 days at 70° C. After cooling, the reaction mixture was evaporated. The residue was partitioned between dichloromethane and water. The organic layer was separated, washed with water, dried, filtered and evaporated. The residue was purified by column chromatography (silica gel; $CH_2Cl_2/CH_3OH$ 95:5). The eluent of the desired fraction was evaporated and the residue was crystallized from acetonitrile (to which a few drops of water were added). The product was filtered off at 0° C. and was dried in vacuo at 40° C., yielding 2.3 parts (55.8%) of cis-4-amino-5-chloro-N-[1-(1,3-dioxolan-2-ylmethyl)-3-methoxy-4-piperidinyl]-2,3-dihydro-7-benzofurancarboxamide; mp. 149.1° C. (comp. 83).

EXAMPLE 11

A mixture of 2.78 parts of 1-(3-chloropropyl)-2-methyl-1H-benzimidazole, 3.3 parts of intermediate 2, 2.04 parts of N,N-diethylethanamine and 94 parts of N,N-dimethylformamide was stirred for 20 hours at 70° C. The reaction mixture was evaporated and water was added to the residue. The product was extracted with dichloromethane (2×) and the combined extracts were washed with water, dried, filtered and evaporated. The residue was crystallized from acetonitrile (to which a few drops of water were added), yielding 2.30 parts (44.6%) of cis-4-amino-5-chloro-2,3-dihydro-N-[3-methoxy-1-[3-(2-methyl-1H-benzimidazol-1-yl)propyl]-4-piperidinyl]-7-benzofurancarboxamide monohydrate; mp. 151.5° C. (comp. 27).

EXAMPLE 12

A mixture of 3.3 parts of intermediate 2, 4.4 parts of ethyl N-(2-oxoethyl)-N-phenylcarbamate, 2 parts of a solution of thiophene in methanol 4% and 198 parts of methanol was hydrogenated at normal pressure and 50° C. with 2 parts of platinum-on-charcoal catalyst 5%. After the calculated amount of hydrogen was taken up, the catalyst was filtered off and the filtrate was evaporated. The residue was diluted with water and the product was extracted with dichloromethane (2×). The combined extracts were dried, filtered and evaporated. The residue was purified by column chromatography (silica gel; $CH_2Cl_2/CH_3OH$ 95:5). The eluent of the desired fraction was evaporated and the residue was suspended in 2,2'-oxybispropane. The product was filtered off and dried, yielding 3.08 parts (58.6%) of ethyl cis-N-[2-[4-[[(4-amino-5-chloro-2,3-dihydro-7-benzofuranyl)carbonyl]amino]-3-methoxy-1-piperidinyl]ethyl]-N-phenylcarbamate hemihydrate; mp. 116.4° C. (comp. 57).

EXAMPLE 13

To a stirred mixture of 3.4 parts of intermediate 7, 2 parts of tetrahydrofuran, 2 parts of a solution of thiophene in methanol 4% and 119 parts of methanol was added dropwise a mixture of 11 ml of an acetaldehyde solution in tetrahydrofuran 10% and 8.9 parts of tetrahydrofuran, during the hydrogenation. After completion of the hydrogenation, the catalyst was filtered off and the filtrate was evaporated. The residue was dissolved in dichloromethane and this solution was washed with water (2×), dried, filtered and evaporated. The residue was recrystallized from acetonitrile. The product was filtered off and dried, yielding 2.66 parts (72.3%) of cis-5-amino-6-chloro-N-(1-ethyl-3-methoxy-4-piperidinyl)-3,4-dihydro-2H-1-benzopyran-8-carboxamide; mp. 153.8° C. (comp. 81).

EXAMPLE 14

A mixture of 3 parts of 1-hexanal, 3.7 parts of intermediate 3, 1 part of a solution of thiophene in methanol 4% and 242.5 parts of 2-methoxyethanol was hydrogenated at normal pressure and at 50° C. with 2 parts of platinum-on-charcoal catalyst 5%. After the calculated mount of hydrogen was taken up, the catalyst was filtered off and the filtrate was evaporated. The residue was purified by column chromatography (silica gel; CH₂Cl₂/CH₃OH (NH₃) 98:2). The eluent of the desired fraction was evaporated and the residue was crystallized from 2,2'-oxybispropane. The product was dried in vacuo at 70° C., yielding 3.20 parts (68.5%) of cis-4-amino-5-chloro-N-(1-hexyl-3-hydroxy-4-piperidinyl)-2,3-dihydro-7-benzofurancarboxamide; mp. 130.4° C. (comp. 8).

EXAMPLE 15

A mixture of 4.5 parts of (1,1-dimethylethyl) (2-oxoethyl)methylcarbamate, 5.5 parts of intermediate 2, 1 parts of a solution of thiophene in methanol 4%, 198 parts of methanol and 2 parts of potassium acetate was hydrogenated at normal pressure and room temperature with 2 parts of palladium-on-charcoal catalyst 10%. After the calculated amount of hydrogen was taken up, the catalyst was filtered off and the filtrate was evaporated. The residue was partitioned between trichloromethane and water. The organic layer was separated, washed with water, dried, filtered and evaporated. The residue was solidified in 2,2'-oxybispropane (to which a few drops of water were added). The product was filtered off at 0° C. and dried in vacuo at 40° C., yielding 6.3 parts (76.7%) of (1,1-dimethylethyl) cis-[2-[4-[(4-amino-5-chloro-2,3-dihydro-7-benzo-furanyl)carbonylamino]-3-methoxy-1-piperidinyl]ethyl]methylcarbamate (comp. 41).

EXAMPLE 16

To a refluxing solution of 17.4 parts of intermediate 2 in 195 parts of 2-propanol were added 4.03 parts of 2-propenenitrile. Stirring at reflux temperature was continued for 18 hours. The reaction mixture was evaporated and the residue was crystallized from 2-propanol. The product was filtered off and dried in vacuo at 60° C., yielding 14.8 parts (73.7%) of cis-4-amino-5-chloro-H-[1-(2-cyanoethyl)-3-methoxy-4-piperidinyl]-2,3-dihydro-7-benzofurancarboxamide; mp. 190.7° C. (comp. 97).

EXAMPLE 17

A solution of 15.7 parts of cis-4-amino-5-chloro-N-[1-(cyanomethyl)-3-methoxy4piperidinyl]-2,3-dihydro-7-benzofurancarboxamide in 178 parts of tetrahydrofuran and 158 parts of methanol was hydrogenated at normal pressure and at room temperature with 6 parts of Raney nickel. After the calculated amount of hydrogen was taken up, the catalyst was filtered off and the filtrate was evaporated. The residue was purified by column chromatography (silica gel; CH₂Cl₂/CH₃OH(NH₃) 93:7). The eluent of the desired fraction was evaporated and the residue was crystallized from acetonitrile (to which a few drops of water were added). The product was filtered off at 0° C. and dried in vacuo at 40° C., yielding 8.5 parts (53.6%) of cis-4-amino-N-[1-(2-aminoethyl)-3-methoxy-4-piperidinyl]-5-chloro-2,3-dihydro-7-benzofurancarboxamide (comp. 35).

EXAMPLE 18

To a cooled (ice-bath) mixture of 3.8 parts of cis-4amino-5-chloro-2,3-dihydro-N-[-3-methoxy-1-[2-(methylamino)-ethyl]-4-piperidinyl]-7-benzofurancarboxamide monohydrate in 104.3 parts of trichloromethane were added 1.3 parts of 1-pyrrolidinecarbonyl chloride. After stirring for 15 min. at 0° C., there were added dropwise 1.3 1 parts of N,N-diethylethanamine, keeping the temperature below 10° C. Stirring was continued for 20 hours at room temperature. The reaction mixture was washed with water, dried, filtered and evaporated. The residue was crystallized from acetonitrile (to which some water was added). The product was filtered off at 0° C. and dried in vacuo at 40° C., yielding 3.3 parts (73.6%) of cis-4-amino-5-chloro-2,3-dihydro-N-[3-methoxy-1-[2-[methyl(1-pyrrolidinylcarbonyl)amino]ethyl]-4-piperidinyl]-7-benzofurancarboxamide monohydrate; mp. 112.0° C. (comp. 43).

EXAMPLE 19

A mixture of 1.4 parts of 2-chloro-3-pyridinecarbonitrile, 3.2 parts of cis-4-amino-N-[1-(4-aminobutyl)-3-methoxy-4-piperidinyl]-5-chloro-2,3-dihydro-7-benzofurancarboxamide, 65.8 parts of N,N-dimethylformamide and 1.3 parts of sodium carbonate was stirred for 20 hours at 70° C. The solvent was evaporated and the residue was dissolved in trichloromethane. The organic layer was washed with water, dried, filtered and evaporated. The residue was purified by column chromatography (silica gel; CHCl₃/CH₃OH (NH₃) 98:2). The eluent of the desired fraction was evaporated and the residue was crystallized from 2,2'-oxybispropane. The product was dried in vacuo at 60° C., yielding 1.44 parts (35.4%)of cis-4-amino-5-chloro-N-[1-[4-[(3-cyano-2-pyridinyl)-amino]butyl]-3-methoxy -4-piperidinyl]-2,3-dihydro-7-benzofurancarboxamide hemihydrate; mp. 129.7° C. (comp. 6).

EXAMPLE 20

A mixture of 1.18 parts of 2-chloro-4(3H)-quinazolinone, 2.40 parts of compound 35 and a minimal amount of N,N-dimethylformamide was stirred for 3 hours at 120° C. After cooling, the reaction mixture was partitioned between dichloromethane and methanol. The organic layer was separated, dried, filtered and evaporated. The residue was purified by column chromatography (silica gel; CH₂Cl₂/CH₃OH 90:10). The eluent of the desired fraction was evaporated and the residue was crystallized from acetonitrile (to which some water was added). The product was filtered off at 0° C. and dried, yielding 0.95 parts (37.5%) of cis-4-amino-5-chloro-2,3-dihydro-N-[-1-[2-[(3,4-dihydro-4-oxo-2-quinazolinyl)amino]ethyl]-3-methoxy-4-piperidinyl]-7-benzofurancarboxamide sesquihydrate; mp. 191.8° C. (comp. 88).

EXAMPLE 21

A mixture of 4.69 parts of cis-4-amino-N-[1-(2-aminoethyl)-3-methoxy-4-piperidinyl]-5-chloro-2,3-dihydro-2,2-dimethyl-7-benzofurancarboxamide dihydrochloride, 1.54 parts of 2-chloro-3-methylpyridazine and 1.68 parts of calciumoxide was stirred for 20 hours at 120° C. After cooling, the reaction mixture was diluted with water and the product was extracted with dichloromethane (3x). The combined extracts were dried, filtered and evaporated. The residue was purified by column chromatography (silica gel; CH₂Cl₂/CH₃OH(NH₃) 95:5). The eluent of the desired fraction was evaporated and the residue was converted into the ethanedioate salt in 2-propanol. The product was filtered off and dried, yielding 1.38 parts (23.1%) of cis-4-amino-5-chloro-2,3-dihydro-N-[-3-methoxy-1-[2-[(3-methyl-2-pyrazinyl)amino]ethyl]-4-piperidinyl-2,2-dimethyl-7-benzofurancarboxamide ethanedioate (1:1) monohydrate; mp. 117.1° C. (comp. 130). A mixture of 5 parts of cis-5-amino-N-[1-(3-aminopropyl)-3-methoxy4-piperidinyl]-6-chloro-3,4-dihydro-2H-1-benzopyran-8-carboxamide, 3.2 parts of 2-methylthio-4-pyrimidinol and 79 parts of acetonitrile was stirred over weekend at reflux temperature. The reaction mixture was evaporated and the residue was partitioned between dichloromethane and ammonia (aq.). The aqueous layer was separated and re-extracted with dichloromethane (2×). The combined dichloromethane layers were dried, filtered and evaporated. The residue was purified by column chromatography (silica gel; $CH_2Cl_2/CH_3OH(NH_3)$ 95:5). The eluent of the two desired fractions was evaporated and the residues were separately crystallized from acetonitrile. The product was filtered off and dried in vacuo at 70° C., yielding a first fraction of 2.22 parts (35.2%) of cis-5-amino-6-chloro-3,4-dihydro-N-[1-[3-[(4-hydroxy-2-pyrimidinyl)amino]propyl-3-methoxy-4-piperidinyl]-2H-1-benzopyran-8-carboxamide hemihydrate; mp. 142.6° C. and a second fraction of 1.00 part (15.9%) of cis-5-amino-6-chloro-3,4-dihydro-E-[1-[3-[(4-hydroxy-2-pyrimidinyl)amino]propyl]-3-methoxy-4-piperidinyl]-2H-1-benzopyran-8-carboxamide hemihydrate; mp. 143.5° C. Total yield: 3.22 parts (51.1%)of product (comp. 128).

EXAMPLE 23

A mixture of 5.4 parts of cis-4-amino-5-chloro-2,3-dihydro-N-[3-methoxy-1-[3-(2-methyl-1,3-dioxolan-2-yl)propyl]4-piperidinyl]-2,2-dimethyl-7-benzofurancarboxamide and 85 ml of an aqueous sulfuric acid solution 1% was stirred for 2 hours at reflux temperature. After cooling, the reaction mixture was basified with ammonia and extracted with dichloromethane (2×). The combined extracts were dried, filtered and evaporated. The residue was purified by column chromatography (silica gel; $CH_2Cl_2/CH_3OH$ 95:5). The eluent of the desired fraction was evaporated and the residue was suspended in 2,2'-oxybispropane. The product was filtered off and dried, yielding 2.4 parts (51.6%) of cis-4-amino-5-chloro-2,3-dihydro-N-[3-methoxy-1-(4-oxopentyl)-4-piperidinyl]-2,2-dimethyl-7-benzofurancarboxamide hemihydrate; mp. 137.7° C. (comp. 112).

EXAMPLE 24

A mixture of 6.3 parts of compound 41, 23.4 parts of 2-propanol, saturated with hydrochloric acid and 198 parts of methanol was stirred for 15 min. at reflux temperature. After cooling, the reaction mixture was evaporated. The residue was taken up in water and the whole was basified with ammonia. The product was extracted with trichloromethane and the extract was dried, filtered and evaporated. The residue was crystallized from acetonitrile (to which a few drops of water were added). The product was filtered off at 0° C. and dried in vacuo at 40° C., yielding 3.8 parts (72.9%) of cis-4-amino-5-chloro-2,3-dihydro-N-[3-methoxy-1-[2-(methylamino)ethyl]-4-piperidinyl]-7-benzofurancarboxamide monohydrate (comp. 42).

The compounds listed in Table 2 were prepared according to similar procedures as described in any of the proceeding examples 5–24.

TABLE 2

$$L^2-(CH_2)_n-N\overbrace{\phantom{xxx}}^{OR^3}-NH-\overset{O}{\underset{\|}{C}}-\overbrace{\phantom{xxx}}^{Cl}-NH_2 \quad \underline{cis}$$
(with —O—A— ring)

| Comp. no. | Ex. no. | L² | n | R³ | —O—A— | base/salt form | mp. (°C.) |
|---|---|---|---|---|---|---|---|
| 1 | 5 | $H_5C_2-N\underset{\|}{\overset{O}{C}}-\text{(benzimidazolyl)}-N-$ | 2 | —CH₃ | —O—(CH₂)₂— | | 173.7 |
| 2 | 5 | (phthalazinone)-N- | 2 | —CH₃ | —O—(CH₂)₂— | | 171.0 |
| 3 | 11 | 4-F—C₆H₄—O— | 3 | —CH₃ | —O—(CH₂)₂— | | 138.6 |
| 4 | 11 | CN— | 3 | —CH₃ | —O—(CH₂)₂— | | — |
| 5 | 17 | H₂N— | 4 | —CH₃ | —O—(CH₂)₂— | | — |
| 6 | 19 | 3-cyano-2-pyridyl-NH— | 4 | —CH₃ | —O—(CH₂)₂— | 1/2 H₂O | 129.7 |
| 7 | 5 | (phthalazinone)-N- | 2 | —H | —O—(CH₂)₂— | | 209.9 |

TABLE 2-continued

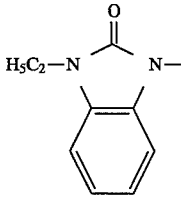

| Comp. no. | Ex. no. | L² | n | R³ | —O—A— | base/salt form | mp. (°C.) |
|---|---|---|---|---|---|---|---|
| 8 | 14 | H— | 6 | —H | —O—(CH$_2$)$_2$— | | 130.4 |
| 9 | 9 | 2-pyridyl- | 1 | —H | —O—(CH$_2$)$_2$— | | 159.4 |
| 10 | 9 | 2-pyridyl- | 1 | —CH$_3$ | —O—(CH$_2$)$_2$— | | 150.4 |
| 11 | 5 | 1-pyrrolidinyl-C(O)— | 3 | —CH$_3$ | —O—(CH$_2$)$_2$— | | 183.7 |
| 12 | 8 | tetrahydro-2-furanyl- | 1 | —CH$_3$ | —O—(CH$_2$)$_2$— | | 172.2 |
| 13 | 5 | 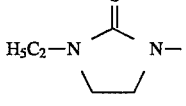 | 3 | —CH$_3$ | —O—(CH$_2$)$_2$— | 1/2 H$_2$O | 134.3 |
| 14 | 14 | H— | 6 | —CH$_3$ | —O—(CH$_2$)$_2$— | | 129.8 |
| 15 | 5 | 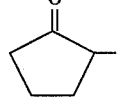 | 2 | —CH$_3$ | —O—(CH$_2$)$_2$— | | 161.8 |
| 16 | 5 | 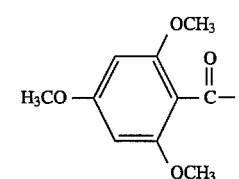 | 2 | —CH$_3$ | —O—(CH$_2$)$_2$— | | 123 |
| 17 | 11 | 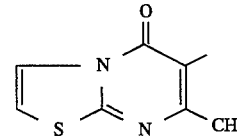 | 3 | —CH$_3$ | —O—(CH$_2$)$_2$— | H$_2$O | 124 |
| 18 | 5 | 2-CH$_3$-1,3-dioxolan-2-yl | 3 | —CH$_3$ | —O—(CH$_2$)$_2$— | H$_2$O | 118.7 |
| 19 | 23 | CH$_3$—C(O)— | 3 | —CH$_3$ | —O—(CH$_2$)$_2$— | | 129.8 |
| 20 | 11 | c.C$_6$H$_{11}$— | 2 | —CH$_3$ | —O—(CH$_2$)$_2$— | H$_2$O | 117.3 |
| 21 | 13 | H— | 2 | —CH$_3$ | —O—(CH$_2$)$_2$— | H$_2$O | 134.7 |
| 22 | 5 | 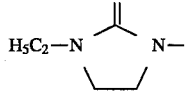 | 2 | —CH$_3$ | —O—(CH$_2$)$_2$— | | 266.0 |
| 23 | 5 | H$_5$C$_2$—N(C(O))N— (imidazolidinone) | 3 | —CH$_3$ | —O—(CH$_2$)$_2$— | | 124.2 |
| 24 | 11 | H$_5$C$_2$—O—C(O)— | 3 | —CH$_3$ | —O—(CH$_2$)$_2$— | H$_2$O | 92.8 |

TABLE 2-continued

[Structure: L²—(CH₂)ₙ—N(piperidine with OR³)—NH—C(=O)—(benzene ring with Cl, NH₂, and O-A bridge), cis]

| Comp. no. | Ex. no. | L² | n | R³ | —O—A— | base/salt form | mp. (°C.) |
|---|---|---|---|---|---|---|---|
| 25 | 5 | H₅C₂—N(C=O)N— (benzimidazolone, N-ethyl) | 3 | —H | —O—(CH₂)₂— |  | 177.2 |
| 26 | 5 | CH₃—N(C=O)N— (benzimidazolone, N-methyl) | 3 | —CH₃ | —O—(CH₂)₂— | 1/2 H₂O | 128.0 |
| 27 | 11 | N=C(CH₃)—N— (2-methylbenzimidazole) | 3 | —CH₃ | —O—(CH₂)₂— | H₂O | 151.5 |
| 28 | 11 | 3,4,5-trimethoxybenzoyl (CH₃O)₃C₆H₂—C(=O)— | 3 | —CH₃ | —O—(CH₂)₂— | H₂O | 147.9 |
| 29 | 5 | H₅C₆—CH₂—N(C=O)N— (N-benzyl benzimidazolone) | 3 | —CH₃ | —O—(CH₂)₂— | H₂O | 124.3 |
| 30 | 6 | 2-methyl-3-methyl-quinazolin-4(3H)-one-2-yl | 2 | —CH₃ | —O—(CH₂)₂— |  | 274.9 |
| 31 | 11 | 2-acetyl-4-fluorophenoxy (F-C₆H₃(C(=O)CH₃)—O—) | 3 | —CH₃ | —O—(CH₂)₂— | H₂O | 111.9 |

TABLE 2-continued

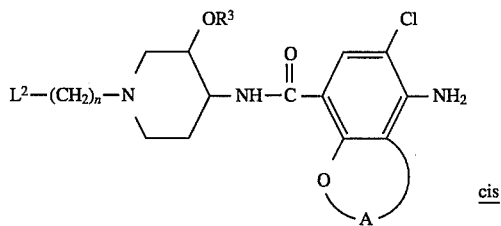

cis

| Comp. no. | Ex. no. | L² | n | R³ | —O—A— | base/salt form | mp. (°C.) |
|---|---|---|---|---|---|---|---|
| 32 | 5 | (pyridinyl-triazinone-N—) | 2 | —CH₃ | —O—(CH₂)₂— | H₂O | 157.3 |
| 33 | 5 | H₇C₃—N(C=O)N— (benzimidazolone) | 3 | —CH₃ | —O—(CH₂)₂— | H₂O | 129.9 |
| 34 | 11 | NC— | 1 | —CH₃ | —O—(CH₂)₂— | | |
| 35 | 17 | H₂N— | 2 | —CH₃ | —O—(CH₂)₂— | | |
| 36 | 18 | H₅C₂—O—C(O)—NH— | 2 | —CH₃ | —O—(CH₂)₂— | 1/2 H₂O | 145.2 |
| 37 | 18 | (H₇C₃)₂—N—C(O)—NH— | 2 | —CH₃ | —O—(CH₂)₂— | | 157.4 |
| 38 | 7 | H₅C₂—N(C=O)N— (benzimidazolone) | 3 | —CH₃ | —O—(CH₂)₂—O— | | 157.8 |
| 39 | 8 | tetrahydro-2-furanyl- | 1 | —CH₃ | —O—(CH₂)₂—O— | | 191.6 |
| 40 | 18 | 2,6-dichlorobenzoyl-NH— | 2 | —CH₃ | —O—(CH₂)₂— | 1/2 H₂O | 145.4 |
| 41 | 15 | (CH₃)₃C—O—C(O)—N(CH₃)— | 2 | —CH₃ | —O—(CH₂)₂— | | |
| 42 | 24 | CH₃—NH— | 2 | —CH₃ | —O—(CH₂)₂— | H₂O | |
| 43 | 18 | pyrrolidinyl-C(O)—N(CH₃)— | 2 | —CH₃ | —O—(CH₂)₂— | H₂O | 112.0 |
| 44 | 9 | H₅C₂—N(C=O)N— (dihydroimidazolone) | 3 | —CH₃ | —O—(CH₂)₂— | | 203.6 |

TABLE 2-continued

[Structure: L²—(CH₂)ₙ—N(piperidine with OR³)—NH—C(=O)—(benzene ring with Cl, NH₂, and O—A bridge), cis]

| Comp. no. | Ex. no. | L² | n | R³ | —O—A— | base/salt form | mp. (°C.) |
|---|---|---|---|---|---|---|---|
| 45 | 5 | H₅C₂—N(C(=O))N— (benzimidazolone) | 4 | —CH₃ | —O—(CH₂)₂— | H₂O | 113.2 |
| 46 | 9 | H₅C₂—N(C(=O))N— (5-chlorobenzimidazolone) | 3 | —CH₃ | —O—(CH₂)₂— | | 180.2 |
| 47 | 11 | HN(C(=O))N— (with CH₂C(=O) ring) | 2 | —CH₃ | —O—(CH₂)₂— | 1/2 H₂O | 202.6 |
| 48 | 15 | H— | 6 | —CH₃ | —O—(CH₂)₂—O— | | 129.7 |
| 49 | 7 | phthalazinone-yl | 2 | —CH₃ | —O—(CH₂)₂—O— | | 171.9 |
| 50 | 11 | 4-F—C₆H₄—O— | 3 | —CH₃ | —O—(CH₂)₂—O— | | 142.3 |
| 51 | 8 | 1,4-benzodioxan-2-ylmethyl | 1 | —CH₃ | —O—(CH₂)₂— | | 239.2 |
| 52 | 12 | 2-furanyl- | 1 | —CH₃ | —O—(CH₂)₂— | H₂O | 87.0 |
| 53 | 12 | chroman-2-yl | 1 | —CH₃ | —O—(CH₂)₂— | | 191.1 |
| 54 | 8 | tetrahydro-2-furanyl- | 2 | —CH₃ | —O—(CH₂)₂— | H₂O | 124.6 |
| 55 | 8 | tetrahydro-2-pyranyl- | 1 | —CH₃ | —O—(CH₂)₂— | | 150.8 |
| 56 | 8 | tetrahydro-2-pyranyl- | 1 | —CH₃ | —O—C(CH₃)₂—CH₂— | | 170.1 |
| 57 | 12 | H₅C₂O—C(=O)—N(C₆H₅)— | 2 | —CH₃ | —O—(CH₂)₂— | 1/2 H₂O | 116.4 |

TABLE 2-continued

[Structure: L²—(CH₂)ₙ—N(piperidine with OR³)—NH—C(=O)—(benzene with Cl, NH₂, and fused O—A ring), cis]

| Comp. no. | Ex. no. | L² | n | R³ | —O—A— | base/salt form | mp. (°C.) |
|---|---|---|---|---|---|---|---|
| 58 | 11 | [imidazolidine-2,4-dione-3-yl-CH₂-] (HN—C(=O)—N—CH₂—C(=O) ring) | 3 | —CH₃ | —O—(CH₂)₂— | HCl | 231.9 |
| 59 | 11 | CH₃—O— | 3 | —CH₃ | —O—(CH₂)₂— | H₂O | 118.3 |
| 60 | 7 | 1-ethyl-2-oxo-benzimidazol-3-yl (H₅C₂—N—C(=O)—N— fused to benzene) | 3 | —CH₃ | —O—C(CH₃)₂—CH₂— | | 187.1 |
| 61 | 7 | 1-n-hexyl-2-oxo-benzimidazol-3-yl (n.H₁₃C₆—N—C(=O)—N— fused to benzene) | 3 | —CH₃ | —O—(CH₂)₂— | H₂O | 103.0 |
| 62 | 5 | 1-benzyl-2-oxo-benzimidazol-3-yl (H₅C₆—CH₂—N—C(=O)—N— fused to benzene) | 3 | —H | —O—(CH₂)₂— | | 216.9 |
| 63 | 8 | tetrahydro-2-furanyl- | 2 | —H | —O—(CH₂)₂— | | 154.8 |
| 64 | 13 | H— | 2 | —H | —O—(CH₂)₂— | | 171.5 |
| 65 | 8 | tetrahydro-2-furanyl- | 1 | —H | —O—(CH₂)₂— | | 186.4 |
| 66 | 11 | HC(O)—NH— | 4 | —CH₃ | —O—(CH₂)₂— | | 189.9 |
| 67 | 11 | (2-methyl-pyridin-4-yl)-O— (CH₃-pyridine-O—) | 3 | —CH₃ | —O—(CH₂)₂— | | 166.1 |
| 68 | 8 | tetrahydro-2-furanyl- | 3 | —CH₃ | —O—(CH₂)₂— | H₂O | 118.0 |
| 69 | 11 | 1-ethyl-2-oxo-imidazo[4,5-b]pyrazin-3-yl (H₅C₂—N—C(=O)—N— fused to pyrazine) | 3 | —CH₃ | —O—(CH₂)₂— | | 146.6 |

TABLE 2-continued

Structure: L²—(CH₂)ₙ—N(piperidine with OR³)—NH—C(=O)—(benzene with Cl, NH₂, and O–A bridge), cis

| Comp. no. | Ex. no. | L² | n | R³ | —O—A— | base/salt form | mp. (°C.) |
|---|---|---|---|---|---|---|---|
| 70 | 11 | H₅C₂—N(C=O)N— fused to pyridine ring | 3 | —CH₃ | —O—(CH₂)₂— | 3/2 H₂O | 130.0 |
| 71 | 5 | H₅C₂—N(C=O)N— fused to benzene ring | 3 | —CH₃ | —O—CH(CH₃)—CH₂— | 1/2 H₂O | 94.2 |
| 72 | 8 | tetrahydro-2-furanyl- | 1 | —CH₃ | —O—CH(CH₃)—CH₂— | 1/2 H₂O | 67.6 |
| 73 | 8 | tetrahydro-2-furanyl- | 4 | —CH₃ | —O—(CH₂)₂— | H₂O | 153.4 |
| 74 | 12 | C₆H₅— | 1 | —CH₃ | —O—(CH₂)₂— | | 129.7 |
| 75 | 11 | H₂C=CH— | 1 | —CH₃ | —O—(CH₂)₂— | H₂O | 142.3 |
| 76 | 8 | tetrahydro-2-furanyl- | 1 | —CH₃ | —O—(CH₂)₃— | | 158.1 |
| 77 | 11 | c.C₃H₅— | 1 | —CH₃ | —O—(CH₂)₂— | | 162.3 |
| 78 | 11 | (CH₃)₂CH—O— | 2 | —CH₃ | —O—(CH₂)₂— | | 121.9 |
| 79 | 7 | H₅C₂—N(C=O)N— fused to benzene ring | 3 | —CH₃ | —O—(CH₂)₃— | | 100.6 |
| 80 | 6 | thiazoline-fused pyrimidinone with CH₃ | 2 | —CH₃ | —O—(CH₂)₂— | | 260.8 |
| 81 | 13 | H— | 2 | —CH₃ | —O—(CH₂)₃— | | 153.8 |
| 82 | 11 | (CH₃)₂CH—O— | 3 | —CH₃ | —O—(CH₂)₂— | H₂O | 93.2 |
| 83 | 10 | 1,3-dioxolanyl- | 1 | —CH₃ | —O—(CH₂)₂— | | 149.1 |
| 84 | 12 | H— | 1 | —CH₃ | —O—(CH₂)₂— | | 214.6 |
| 85 | 12 | c.C₆H₁₁— | 0 | —CH₃ | —O—(CH₂)₂— | H₂O | 139.3 |
| 86 | 5 | N-methyl quinazoline-2,4-dione | 3 | —CH₃ | —O—(CH₂)₂— | | 264.2 |
| 87 | 11 | (CH₃)₂CH—O— | 3 | —CH₃ | —O—C(CH₃)₂—CH₂— | HCl/H₂O | 151.0 |

TABLE 2-continued
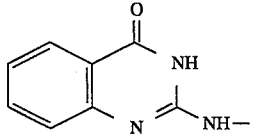
| Comp. no. | Ex. no. | L² | n | R³ | —O—A— | base/salt form | mp. (°C.) |
|---|---|---|---|---|---|---|---|
| 88 | 20 | 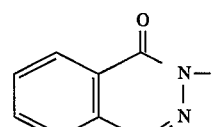 | 2 | —CH₃ | —O—(CH₂)₂— | 3/2 H₂O | 191.8 |
| 89 | 9 | 2-CH₃-1,3-dioxolan-2-yl- | 3 | —CH₃ | —O—C(CH₃)₂—CH₂— | (COOH)₂ | 135.1 |
| 90 | 11 | 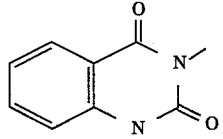 | 3 | —CH₃ | —O—(CH₂)₂— | | 210.7 |
| 91 | 11 | 2-pyridyl- | 1 | —CH₃ | —O—(CH₂)₃— | H₂O | 96.2 |
| 92 | 5 | 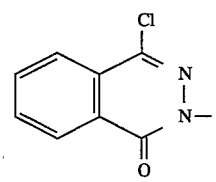 | 2 | —CH₃ | —O—(CH₂)₂— | 3/2 H₂O | 271.7 |
| 93 | 5 | 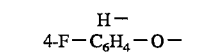 | 2 | —CH₃ | —O—(CH₂)₂— | | 230.5 |
| 94 | 13 | H— | 2 | —CH₃ | —O—C(CH₃)₂—CH₂— | | 174.4 |
| 95 | 11 | 4-F—C₆H₄—O— | 3 | —CH₃ | —O—(CH₂)₃— | | 134.2 |
| 96 | 7 | 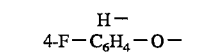 | 2 | —CH₃ | —O—(CH₂)₃— | | 219.1 |
| 97 | 16 | NC— | 2 | —CH₃ | —O—(CH₂)₂— | | |
| 98 | 17 | H₂N— | 3 | —CH₃ | —O—(CH₂)₂— | | 185.9 |
| 99 | 11 | (CH₃)₂CH—O— | 2 | —CH₃ | —O—(CH₂)₃— | | 141.4 |
| 100 | 11 | NC— | 1 | —CH₃ | —O—(CH₂)₃— | | 175 |
| 101 | 17 | H₂N— | 2 | —CH₃ | —O—(CH₂)₃— | | 138.5 |
| 102 | 22 | 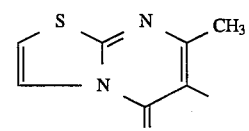 | 3 | —CH₃ | —O—(CH₂)₂— | 1/2 H₂O | 188.6 |
| 103 | 11 | (CH₃)₂CH—O— | 3 | —CH₃ | —O—(CH₂)₃— | HCl/H₂O | 200 |

TABLE 2-continued

[Structure: L²–(CH₂)ₙ–N (piperidine with OR³) –NH–C(=O)–(benzene with Cl and NH₂)–O–A, cis]

| Comp. no. | Ex. no. | L² | n | R³ | —O—A— | base/salt form | mp. (°C.) |
|---|---|---|---|---|---|---|---|
| 104 | 21 | 3-methyl-2-(pyrazinyl)amino– (pyrazine with CH₃ and NH—) | 2 | —CH₃ | —O—(CH₂)₃— | | 200.2 |
| 105 | 16 | NC— | 2 | —CH₃ | —O—C(CH₃)₂—CH₂— | | |
| 106 | 17 | H₂N— | 3 | —CH₃ | —O—C(CH₃)₂—CH₂— | 2(COOH)₂ | |
| 107 | 22 | 4-hydroxy-2-pyrimidinyl-NH— | 3 | —CH₃ | —O—C(CH₃)₂—CH₂— | | 163.8 |
| 108 | 16 | NC— | 1 | —CH₃ | —O—C(CH₃)₂—CH₂— | | 183.3 |
| 109 | 11 | 2-CH₃-1,3-dioxolan-2-yl- | 3 | —CH₃ | —O—(CH₂)₃— | | 127.8 |
| 110 | 23 | CH₃—C(O)— | 3 | —CH₃ | —O—(CH₂)₃— | (COOH)₂ | 168.4 |
| 111 | 9 | 4-F—C₆H₄—O— | 3 | —CH₃ | —O—C(CH₃)₂—CH₂— | (COOH)₂ | 140.3 |
| 112 | 23 | CH₃—C(O)— | 3 | —CH₃ | —O—C(CH₃)₂—CH₂— | 1/2 H₂O | 137.7 |
| 113 | 12 | 4-F—C₆H₄— | 1 | —CH₃ | —O—C(CH₃)₂—CH₂— | | 186.7 |
| 114 | 11 | 4-oxo-benzo[d][1,2,3]triazin-3-yl— | 3 | —CH₃ | —O—C(CH₃)₂—CH₂— | (COOH)₂ 1/2 H₂O | 185.1 |
| 115 | 5 | 1-oxo-phthalazin-2-yl— | 2 | —CH₃ | —O—(CH₂)₃— | H₂O | 111.5 |
| 116 | 10 | 1,3-dioxolanyl- | 1 | —CH₃ | —O—C(CH₃)₂—CH₂— | (COOH)₂ | 184.9 |
| 117 | 7 | 3-ethyl-2-oxo-imidazolidin-1-yl— | 3 | —CH₃ | —O—(CH₂)₃— | | 165.2 |
| 118 | 7 | 6-chloro-3-oxo-pyridazin-2-yl— | 2 | —CH₃ | —O—(CH₂)₃— | | 170.9 |
| 119 | 8 | c.C₆H₁₁—O— | 3 | —CH₃ | —O—(CH₂)₃— | | 136.4 |
| 120 | 8 | c.C₆H₁₁—O— | 3 | —CH₃ | —O—C(CH₃)₂—CH₂— | (COOH)₂ | 173.0 |
| 121 | 9 | 3-ethyl-2-oxo-imidazolidin-1-yl— | 3 | —CH₃ | —O—C(CH₃)₂—CH₂— | (COOH)₂ | 208.0 |
| 122 | 16 | NC— | 2 | —CH₃ | —O—(CH₂)₃— | | |

TABLE 2-continued

Structure: L²—(CH₂)ₙ—N[piperidine with OR³]—NH—C(=O)—[benzene ring with Cl, NH₂, and fused O-A ring], cis

| Comp. no. | Ex. no. | L² | n | R³ | —O—A— | base/salt form | mp. (°C.) |
|---|---|---|---|---|---|---|---|
| 123 | 17 | H₂N— | 3 | —CH₃ | —O—(CH₂)₃— | | 159.6 |
| 124 | 11 | 3-methyl-4-oxo-3,4-dihydrobenzo[d][1,2,3]triazin-yl | 3 | —CH₃ | —O—(CH₂)₃— | | 208.6 |
| 125 | 18 | CH₃—C(O)—NH— | 3 | —CH₃ | —O—(CH₂)₃— | | 182.3 |
| 126 | 21 | (3-methylpyrazin-2-yl)NH— | 3 | —CH₃ | —O—(CH₂)₃— | H₂O | 131.4 |
| 127 | 7 | thiazolo-pyrimidinone with CH₃ groups | 2 | —CH₃ | —O—C(CH₃)₂—CH₂— | H₂O | 159.5 |
| 128 | 22 | (4-hydroxypyrimidin-2-yl)NH— | 3 | —CH₃ | —O—(CH₂)₃— | 1/2 H₂O | 143.5 |
| 129 | 17 | H₂N— | 2 | —CH₃ | —O—C(CH₃)₂—CH₂— | 2 HCl | |
| 130 | 21 | (3-methylpyrazin-2-yl)NH— | 2 | —CH₃ | —O—C(CH₃)₂—CH₂— | (COOH)₂ | 117.1 |
| 131 | 5 | 6-phenyl-2-methyl-3-oxo-2,3-dihydropyridazin-yl | 2 | —CH₃ | —O—(CH₂)₃— | | 158.2 |
| 132 | 5 | 6-methyl-2-methyl-3-oxo-2,3-dihydropyridazin-yl | 2 | —CH₃ | —O—(CH₂)₃— | | 195.6 |

TABLE 2-continued

Structure: L²—(CH₂)ₙ—N[piperidine with OR³]—NH—C(=O)—[benzene with Cl, NH₂, and O-A bridge] cis

| Comp. no. | Ex. no. | L² | n | R³ | —O—A— | base/salt form | mp. (°C.) |
|---|---|---|---|---|---|---|---|
| 133 | 11 | 3,4,5-trimethoxybenzoyl | 3 | —CH₃ | —O—C(CH₃)₂—CH₂— | 2(COOH)₂ 1/2 H₂O | 186.4 |
| 134 | 12 | H— | 1 | —CH₃ | —O—(CH₂)₃— | | 184.9 |
| 135 | 7 | 3-chloro-6-oxopyridazin-1-yl | 2 | —CH₃ | —O—C(CH₃)₂—CH₂— | | 183.4 |
| 136 | 7 | 3-chloro-6-oxopyridazin-1-yl | 3 | —CH₃ | —O—(CH₂)₃— | | 149.5 |
| 137 | 11 | CH₃—O— | 3 | —CH₃ | —O—(CH₂)₃— | | 134.1 |
| 138 | 11 | 3,4,5-trimethoxybenzoyl | 3 | —CH₃ | —O—(CH₂)₃— | (COOH)₂ | 223.6 |
| 139 | 12 | H— | 1 | —CH₃ | —O—C(CH₃)₂—CH₂— | (COOH)₂ 1/2 H₂O | 215.2 |
| 140 | 21 | 2-guanidinobenzoyl | 3 | —CH₃ | —O—C(CH₃)₂—CH₂— | 1/2 H₂O | 185.6 |
| 141 | 5 | 4-oxoquinazolin-3-yl | 2 | —CH₃ | —O—C(CH₃)₂—CH₂— | | 122.6 |
| 142 | 21 | 2-guanidinobenzoyl | 3 | —CH₃ | —O—(CH₂)₃— | 1/2 H₂O | 164.2 |

EXAMPLE 25

The compounds listed in Table 3 are prepared according to similar procedures as described in any of the proceeding examples.

TABLE 3

Structure: L²—(CH₂)ₙ—N(piperidine with OR³)—NH—C(=O)—[benzene ring with Cl, NH₂, and fused —O—A— ring], cis

| Comp. no. | L² | n | R³ | —O—A— |
|---|---|---|---|---|
| 143 | 2,3,4-trimethoxyphenyl-C(=O)-(1-methyl-triazol-5-yl)- | 0 | —CH₃ | —O—(CH₂)₂— |
| 144 | i.C₃H₇—C(=O)— | 3 | CH₃ | —O—(CH₂)₂— |
| 145 | 1-ethyl-2-thioxo-benzimidazol-3-yl— | 3 | CH₃ | —O—(CH₂)₂— |
| 146 | C₆H₅—N(CH₃)—C(=O)— | 3 | CH₃ | —O—(CH₂)₂— |
| 147 | i.C₃H₇—NH—C(=O)—NH— | 2 | CH₃ | —O—(CH₂)₂— |
| 148 | pyridin-3-yl—O— | 2 | CH₃ | —O—(CH₂)₂— |
| 149 | cyclohexyl— | 2 | CH₃ | —O—(CH₂)₂— |
| 150 | tetrahydrofuran-2-yl— | 1 | CH₃ | —O—C(CH₃)₂—(CH₂)₂— |
| 151 | 4-F—C₆H₄—O— | 3 | CH₃ | —O—C(CH₃)₂—(CH₂)₂— |
| 152 | thiazolo[pyrimidinone with CH₃] | 2 | CH₃ | —O—C(CH₃)₂—(CH₂)₂— |
| 153 | (CH₃)₂CH—O— | 3 | CH₃ | —O—C(CH₃)₂—(CH₂)₂— |

TABLE 3-continued

[Structure: L²—(CH₂)ₙ—N(piperidine with OR³)—NH—C(=O)—(benzene with Cl, NH₂, and O-A bridge) cis]

| Comp. no. | L² | n | R³ | —O—A— |
|---|---|---|---|---|
| 154 | tetrahydrofuran-2-yl (O in 5-ring) | 1 | CH₃ | —O—C(CH₃)₂—(CH₂)₃— |
| 155 | 4-F—C₆H₄—O— | 3 | CH₃ | —O—C(CH₃)₂—(CH₂)₃— |
| 156 | (thiazolyl-methyl-pyrimidinone group) | 2 | CH₃ | —O—C(CH₃)₂—(CH₂)₃— |
| 157 | (CH₃)₂CH—O— | 3 | CH₃ | —O—C(CH₃)₂—(CH₂)₃— |
| 158 | tetrahydrofuran-2-yl | 1 | CH₃ | —O—(CH₂)₄— |
| 159 | 4-F—C₆H₄—O— | 3 | CH₃ | —O—(CH₂)₄— |
| 160 | (thiazolyl-methyl-pyrimidinone group) | 2 | CH₃ | —O—(CH₂)₄— |
| 161 | (CH₃)₂CH—O— | 3 | CH₃ | —O—(CH₂)₄— |

C. Pharmacological examples

The useful gastrointestinal motility stimulating properties of the compounds of the present invention and in particular their capability to enhance the contractility of the colon can be demonstrated in the following test.

EXAMPLE 26

Colon ascendents induced contractions.

The experiment was conducted according to similar procedures as described in The Journal of Pharmacology and Experimental Therapeutics, 234, 776–783 (1985). Colon segments, 4.5 cm long, were vertically suspended with a preload of 2 g in 100 ml of a De Jalon solution [KCl 5.6 mM; CaCl₂.2H₂O 0.54 mM; NaHCO₃ 5.9 mM; NaCl 154.1 mM; glucose 2.8 mM] by 37.5° C. and gassed with a mixture of 95% O₂ and 5% CO₂. Contractions were measured isotonically with a HP 7 DCDT-1000, JSID Displacement Transducer Control Unit.

After a stabilization period of about 20 minutes, 3.4×10⁻⁶M methacholine was given at a time interval of 15 minutes. When reproducible contractions were obtained, the test compound was administered to the bathing solution. The compound effect was followed for 10 minutes and expressed relative to the maximal concentrations induced by 3.4×10⁻⁶M methacholine. The % effect for a representative number of compounds of formula (I) is depicted hereunder in Table 4.

TABLE 4

| Comp. No. | Dose $1.10^{-6}$M | Dose $1.10^{-7}$M |
|---|---|---|
| 1 | +48% | +42% |
| 2 | +32% | +31% |
| 3 | +49% | +39% |
| 5 | +34% | +31% |
| 8 | +45% | +27% |
| 11 | +30% | +26% |
| 13 | +43% | +40% |
| 14 | +52% | +41% |
| 26 | +47% | +37% |
| 33 | +34% | +25% |
| 38 | +33% | +27% |
| 40 | +22% | +32% |
| 43 | +36% | +20% |
| 46 | +26% | +30% |
| 47 | +28% | +25% |
| 48 | +37% | +29% |
| 53 | +30% | +28% |
| 57 | +27% | +25% |
| 66 | +28% | +21% |
| 68 | +41% | +26% |

TABLE 4-continued

| Comp. No. | Dose $1.10^{-6}$M | Dose $1.10^{-7}$M |
|---|---|---|
| 69 | +24% | +29% |
| 70 | +31% | +24% |
| 73 | +27% | +24% |
| 76 | +24% | +20% |
| 79 | +29% | +36% |
| 80 | +36% | +23% |
| 86 | +29% | +24% |
| 95 | +35% | +24% |
| 96 | +34% | +26% |
| 118 | +25% | +29% |
| 132 | +44% | +29% |

D. Composition Examples

EXAMPLE 27

ORAL DROPS

500 Parts of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 parts of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

EXAMPLE 28

ORAL SOLUTION

9 Parts of methyl 4-hydroxybenzoate and 1 part of propyl 4-hydroxybenzoate were dissolved in 4 l of boiling purified water. In 3 l of this solution were dissolved fast 10 parts of 2,3-dihydroxybutanedioic acid and thereafter 20 parts of the A.I. The latter solution was combined with the remaining part of the former solution and 12 l 1,2,3-propanetriol and 3 l of sorbitol 70% solution were added thereto. 40 Parts of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 29

CAPSULES

20 Parts of the A.I., 6 parts sodium lauryl sulfate, 56 parts starch, 56 parts lactose, 0.8 parts colloidal silicon dioxide, and 1.2 parts magnesium stearate were vigorously stirred together. The resulting mixture was subsequently fried into 1000 suitable hardened gelatin capsules, comprising each 20 mg of the active ingredient

EXAMPLE 30

FILM-COATED TABLETS

Preparation of tablet core

A mixture of 100 parts of the A.I., 570 parts lactose and 200 parts starch was mixed well and thereafter humidified with a solution of 5 parts sodium dodecyl 1 sulfate and 10 parts polyvinylpyrrolidone (Kollidon-K 90®) in about 200 ml of water. The wet powder mixture was sieved, dried and sieved again. Then there was added 100 parts micro-crystalline cellulose (Avicel®) and 15 parts hydrogenated vegetable oil (Sterotex®). The whole was mixed well and compressed into tablets, giving 10.000 tablets, each containing 10 mg of the active ingredient Coating To a solution of 10 parts methyl cellulose (Methocel 60 HG®) in 75 ml of denaturated ethanol there was added a solution of 5 parts of ethyl cellulose (Ethocel 22 cps®) in 150 ml of dichloromethane. Then there were added 75 ml of dichloromethane and 2.5 ml 1,2,3-propanetriol. 10 Parts of polyethylene glycol was molten and dissolved in 75 ml of dichloromethane. The latter solution was added to theformer and then there were added 2.5 parts of magnesium octadecanoate, 5 parts of polyvinylpyrrolidone and 30 ml of concentrated colour suspension (Opaspray K-1-2109®) and the whole was homogenated. The tablet cores were coated with the thus obtained mixture in a coating apparatus.

EXAMPLE 31

INJECTABLE SOLUTION 1.8 Parts methyl 4-hydroxybenzoate and 0.2 parts propyl 4-hydroxybenzoate were dissolved in about 0.5 l of boiling water for injection. After cooling to about 50° C. there were added while stirring 4 parts lactic acid, 0.05 parts propylene glycol and 4 parts of the A.I.. The solution was cooled to room temperature and supplemented with water for injection q.s. ad 1 l, giving a solution comprising 4 mg/ml of A.I.. The solution was sterilized by filtration (U.S.P. XVII p. 811) and filled in sterile containers.

EXAMPLE 32

SUPPOSITORIES

3 Parts A.I. was dissolved in a solution of 3 parts 2,3-dihydroxybutanedioic acid in 25 ml polyethylene glycol 400. 12 Parts surfactant (SPAN®) and triglycerides (Witepsol 555®) q.s. ad 300 parts were molten together. The latter mixture was mixed well with the former solution. The thus obtained mixture was poured into moulds at a temperature of 37°–38° C. to form 100 suppositories each containing 30 mg/ml of the A.I.

EXAMPLE 33

INJECTABLE SOLUTION

60 Parts of A.I. and 12 parts of benzylalcohol were mixed well and sesame oil was added q.s. ad 1 l, giving a solution comprising 60 mg/ml of A.I. The solution was sterilized and filled in sterile containers.

We claim:

1. A compound of the formula:

$$L-N \begin{pmatrix} OR^3 \\ \end{pmatrix} - N(R^4) - C(=O) - \begin{pmatrix} R^1 \\ R^2 \end{pmatrix} \quad (I)$$

(with fused O–A ring)

an N-oxide form, a pharmaceutically acceptable salt thereof, or a stereochemically isomeric form thereof, wherein:

A represents a group of the formula:

$$-CH_2-O- \quad \text{(a-4)},$$

$$-CH_2-CH_2-O- \quad \text{(a-5), or}$$

—CH$_2$—CH$_2$—CH$_2$—O—      (a-6), wherein one or two hydrogen atoms in said groups (a-4) to (a-6) may be replaced by a C$_{1-6}$alkyl group;

R$^1$ represents hydrogen, halo, C$_{1-6}$alkylsulfonyl, or aminosulfonyl;

R$^2$ represents hydrogen, amino, mono- or di(C$_{1-6}$alkyl)amino, arylC$_{1-6}$alkylamino, or C$_{1-6}$alkylcarbonylamino;

R$^3$ and R$^4$ each independently represent hydrogen or C$_{1-6}$alkyl; and

L represents a group of the formula:

—Alk—R$^5$      (b-1); or

—Alk—X—R$^6$      (b-2);

wherein:
each Alk represents C$_{1-6}$alkanediyl;
R$^5$ and R$^6$ represent Het; and
X represents O, S, SO$^2$, or NR$^7$ wherein R$^7$ represents hydrogen, C$_{1-6}$alkyl, or aryl;
wherein in the foregoing:
Het represents a group of the formula:

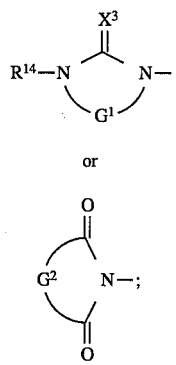

(d-1)

or (d-2)

wherein:
X$^3$ represent O or S;
R$^{14}$ represents hydrogen, C$_{1-6}$alkyl or arylC$_{1-6}$alkyl;
R$^{15}$ represents hydrogen, halo, C$_{1-6}$alkyl or aryl;
G$^1$ represents —CH$_2$—CH$_2$—, —CH=CH—, —N=N—, or —CO—CH$_2$—, wherein one or two hydrogen atoms each independently may be replaced by C$_{1-6}$alkyl;
G$^2$ represents —CH$_2$—CH$_2$—or —CH$_2$—N(R$^{14}$)—, wherein R$^{14}$ is as defined above and wherein one or two hydrogen atoms each independently may be replaced by C$_{1-6}$alkyl; and aryl represents phenyl or phenyl substituted with 1, 2, or 3 substituents each independently selected from the group consisting of halo, hydroxy, C$_{1-6}$alkyl, C$_{1-6}$alkyloxy, aminosulfonyl, C$_{1-6}$alkylcarbonyl, nitro, trifluoromethyl, amino, and aminocarbonyl.

2. A compound according to claim 1 wherein R$^1$ represents hydrogen or halo, R$^2$ represents hydrogen or amino, R$^3$ represents hydrogen or C$_{1-4}$alkyl, and R$^4$ represents hydrogen.

3. A compound according to claim 1 wherein the substituents on the 3 and 4 position of the piperidine ring have the cis-configuration.

4. A compound according to claim 1 wherein R$^1$ is halo, R$^2$ is amino, R$^3$ is C$_{1-4}$alkyl, R$^4$ is hydrogen.

5. A pharmaceutical composition comprising an inert carrier and as active ingredient a gastrointestinal motility stimulating amount of a compound as claimed in any of claims 1-4.

6. A method of treating warm-blooded animals suffering from a decreased peristalsis of the gastrointestinal system, which method comprises the systemic administration to said warm blooded animals of an effective gastrointestinal stimulating amount of a compound as claimed in any of claims 1-4.

7. A compound of the formula:

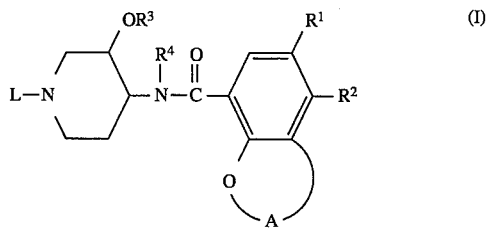

(I)

an N-oxide form, a pharmaceutically acceptable salt thereof, or a stereochemically isomeric form thereof, wherein:

A represents a group of the formula:

—CH$_2$—O—      (a-4),

—CH$_2$—CH$_2$—O—      (a-5), or

—CH$_2$—CH$_2$—CH$_2$—O—      (a-6), wherein one or two hydrogen atoms in said groups (a-4) to (a-6) may be replaced by a C$_{1-6}$alkyl group;

R$^1$ represents hydrogen, halo, C$_1$alkylsulfonyl, or aminosulfonyl;

R$^2$ represents hydrogen, amino, mono- or di(C$_{1-6}$alkyl)amino, arylC$_{1-6}$alkylamino, or C$_{1-6}$alkylcarbonylamino;

R$^3$ and R$^4$ each independently represent hydrogen or C$_{1-6}$alkyl; and

L represents a group of the formula:

—Alk—R$^5$      (b-1); or

—Alk—X—R$^6$      (b-2);

wherein:
each Alk represents C$_{1-6}$alkanediyl;
R$^5$ and R$^6$ represent Het; and
X represents O, S, SO$^2$, or NR$^7$ wherein R$^7$ represents hydrogen, C$_{1-6}$alkyl, or aryl;
wherein in the foregoing:
Het represents a group of the formula:

(d-1)

wherein:
X$^3$ represent O or S;
R$^{14}$ represents hydrogen, C$_{1-6}$alkyl or arylC$_{1-6}$alkyl;
G$^1$ represents —CH$_2$—CH$_2$—CH$_2$—, wherein one or two hydrogen atoms each independently may be replaced by C$_{1-6}$alkyl; and aryl represents phenyl or phenyl substituted with 1, 2, or 3 substituents each independently selected from the group consisting of halo, hydroxy, C$_{1-6}$alkyl, C$_{1-6}$alkyloxy, aminosulfonyl, C$_{1-6}$alkylcarbonyl, nitro, trifluoromethyl, amino, and aminocarbonyl.

8. A compound according to claim 7 wherein $R^1$ represents hydrogen or -halo, $R^2$ represents hydrogen or amino, $R^3$ represents hydrogen or $C_{1-4}$alkyl, and $R^4$ represents hydrogen.

9. A compound according to claim 7 where in the substituents on the 3 and 4 position of the piperidine ring have the cis-configuration.

10. A compound according to claim 7 wherein $R^1$ is halo, $R^2$ is amino, $R^3$ is $C_{1-4}$alkyl, $R^4$ is hydrogen.

11. A pharmaceutical composition comprising an inert carrier and as active ingredient a gastrointestinal motility stimulating amount of a compound as claimed in any of claims 7–10.

12. A method of treating warm-blooded animals suffering from a decreased peristalsis of the gastrointestinal system, which method comprises the systemic administration to said warm blooded animals of an effective gastrointestinal stimulating amount of a compound as claimed in any of claims 7–10.

13. A compound of the formula:

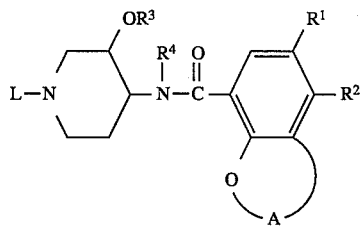

an N-oxide form, a pharmaceutically acceptable salt thereof, or a stereochemically isomeric form thereof, wherein:

A represents a group of the formula:

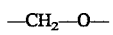      (a-4),

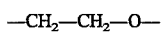      (a-5), or

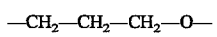      (a-6), wherein one or two hydrogen atoms in said groups (a-4) to (a-6) may be replaced by a $C_{1-6}$alkyl group;

$R^1$ represents hydrogen, halo, $C_{1-6}$alkylsulfonyl, or aminosulfonyl;

$R^2$ represents hydrogen, amino, mono- or di($C_{1-6}$alkyl) amino, aryl$C_{1-6}$alkylamino, or $C_{1-6}$alkylcarbonylamino;

$R^3$ and $R^4$ each independently represent hydrogen or $C_{1-6}$alkyl; and

L represents a group of the formula:

      (b-1); or

      (b-2);

wherein:
each Alk represents $C_{1-6}$alkanediyl;
$R^5$ and $R^6$ represent Het; and
X represents O, S, $SO^2$, or $NR^7$ wherein $R^7$ represents hydrogen, $C_{1-6}$alkyl, or aryl;

wherein in the foregoing:

Het represents a group of the formula:

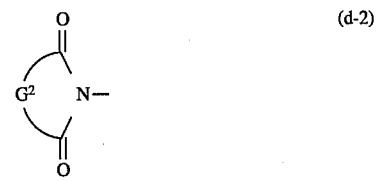      (d-2)

wherein:
$G^2$ represents —$CH_2$—$CH_2$—$CH_2$—, wherein one or two hydrogen atoms each independently may be replaced by $C_{1-6}$alkyl; and aryl represents phenyl or phenyl substituted with 1, 2, or 3 substituents each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, and aminocarbonyl.

14. A compound according to claim 13 wherein $R^1$ represents hydrogen or halo, $R^2$ represents hydrogen or amino, $R^3$ represents hydrogen or $C_{1-4}$alkyl, and $R^4$ represents hydrogen.

15. A compound according to claim 13 wherein the substituents on the 3 and 4 position of the piperidine ring have the cis-configuration.

16. A compound according to claim 13 wherein $R^1$ is halo, $R^2$ is amino, $R^3$ is $C_{1-4}$alkyl, $R^4$ is hydrogen.

17. A pharmaceutical composition comprising an inert carrier and as active ingredient a gastrointestinal motility stimulating amount of a compound as claimed in any of claims 13–16.

18. A method of treating warm-blooded animals suffering from a decreased peristalsis of the gastrointestinal system, which method comprises the systemic administration to said warm blooded animals of an effective gastrointestinal stimulating amount of a compound as claimed in any of claims 13–16.

19. A compound of the formula:

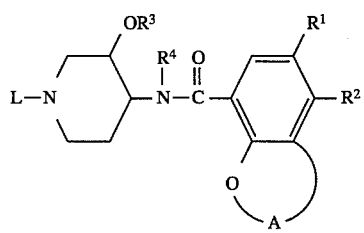

an N-oxide form, a pharmaceutically acceptable salt thereof, or a stereochemically isomeric form thereof, wherein:

A represents a group of the formula:

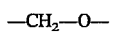      (a-4),

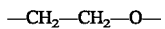      (a-5), or

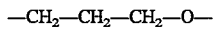      (a-6), wherein one or two hydrogen atoms in said groups (a-4) to (a-6) may be replaced by a $C_{1-6}$alkyl group;

$R^1$ represents hydrogen, halo, $C_{1-6}$alkylsulfonyl, or aminosulfonyl;

$R^2$ represents hydrogen, amino, mono- or di($C_{1-6}$alkyl) amino, aryl$C_{1-6}$alkylamino, or $C_{1-6}$alkylcarbonylamino;

$R^3$ and $R^4$ each independently represent hydrogen or $C_{1-6}$alkyl; and

L represents a group of the formula:

—Alk—R⁵    (b-1); or

—Alk—X—R⁶   (b-2);

wherein:
each Alk represents $C_{1-6}$alkanediyl;
$R^5$ and $R^6$ represent Het; and
X represents O, S, $SO^2$, or $NR^7$ wherein $R^7$ represents hydrogen, $C_{1-6}$alkyl, or aryl;
wherein in the foregoing:
Het represents a group of the formula:

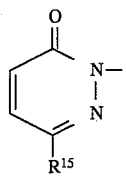   (d-3)

wherein:
represents hydrogen, halo, $C_{1-6}$alkyl or aryl; and
aryl represents phenyl or phenyl substituted with 1, 2, or 3 substituents each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, and aminocarbonyl.

20. A compound according to claim 19 wherein $R^1$ represents hydrogen or halo, $R^2$ represents hydrogen or amino, $R^3$ represents hydrogen or $C_{1-4}$alkyl, and $R^4$ represents hydrogen.

21. A compound according to claim 19 wherein the substituents on the 3 and 4 position of the piperidine ring have the cis-configuration.

22. A compound according to claim 19 wherein $R^1$ is halo, $R^2$ is amino, $R^3$ is $C_{1-4}$alkyl, $R^4$ is hydrogen.

23. A pharmaceutical composition comprising an inert carrier and as active ingredient a gastrointestinal motility stimulating amount of a compound as claimed in any of claims 19–22.

24. A method of treating warm-blooded animals suffering from a decreased peristalsis of the gastrointestinal system, which method comprises the systemic administration to said warm blooded animals of an effective gastrointestinal stimulating amount of a compound as claimed in any of claims 19–22.

25. A compound of the formula:

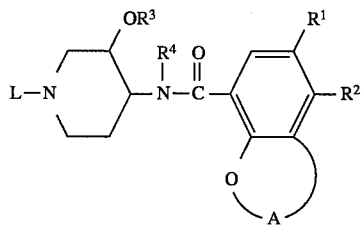   (I)

an N-oxide form, a pharmaceutically acceptable salt thereof, or a stereochemically isomeric form thereof, wherein:
A represents a group of the formula:

—$CH_2$—O—    (a-4),

—$CH_2$—$CH_2$—O—    (a-5), or

—$CH_2$—$CH_2$—$CH_2$—O—    (a-6), wherein one or two hydrogen atoms in said groups (a-4) to (a-6) may be replaced by a $C_{1-6}$alkyl group;

$R^1$ represents hydrogen, halo, $C_{1-6}$alkylsulfonyl, or aminosulfonyl;

$R^2$ represents hydrogen, amino, mono- or di($C_{1-6}$alkyl) amino, aryl$C_{1-6}$alkylamino, or $C_{1-6}$alkylcarbonylamino;

$R^3$ and $R^4$ each independently represent hydrogen or $C_{1-6}$alkyl; and

L represents a group of the formula:

—Alk—R⁵    (b-1); or

—Alk—X—R⁶   (b-2);

wherein:
each Alk represents $C_{1-6}$alkanediyl;
$R^5$ and $R^6$ represent Het; and
X represents O, S, $SO^2$ or $NR^7$ wherein $R^7$ represents hydrogen, $C_{1-6}$alkyl, or aryl;
wherein in the foregoing:
Het represents a group of the formula:

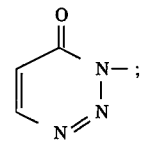   (d-4)

and aryl represents phenyl or phenyl substituted with 1, 2, or 3 substituents each independently selected from the group consisting of halo, hydroxy, $C_{1-6}$alkyl, $C_{1-6}$alkyloxy, aminosulfonyl, $C_{1-6}$alkylcarbonyl, nitro, trifluoromethyl, amino, and aminocarbonyl.

26. A compound according to claim 25 wherein $R^1$ represents hydrogen or halo, $R^2$ represents hydrogen or amino, $R^3$ represents hydrogen or $C_{1-4}$alkyl, and $R^4$ represents hydrogen.

27. A compound according to claim 25 wherein the substituents on the 3 and 4 position of the piperidine ring have the cis-configuration.

28. A compound according to claim 25 wherein $R^1$ is halo, $R^2$ is amino, $R^3$ is $C_{1-4}$alkyl, $R^4$ is hydrogen.

29. A pharmaceutical composition comprising an inert carrier and as active ingredient a gastrointestinal motility stimulating amount of a compound as claimed in any of claims 25–28.

30. A method of treating warm-blooded animals suffering from a decreased peristalsis of the gastrointestinal system, which method comprises the systemic administration to said warm blooded animals of an effective gastrointestinal stimulating amount of a compound as claimed in any of claims 25–28.

* * * * *